(12) United States Patent
Qing et al.

(10) Patent No.: US 12,697,598 B2
(45) Date of Patent: *Aug. 4, 2026

(54) APPARATUS AND METHODS FOR SYNTHESIZING BIOPOLYMERS

(71) Applicant: Arizona Board of Regents on behalf of Arizona State University, Scottsdale, AZ (US)

(72) Inventors: Quan Qing, Chandler, AZ (US); Ching-wei Tsao, Tempe, AZ (US); Peiming Zhang, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 108 days.

This patent is subject to a terminal disclaimer.

(21) Appl. No.: 18/732,594

(22) Filed: Jun. 3, 2024

(65) Prior Publication Data

US 2025/0001384 A1 Jan. 2, 2025

Related U.S. Application Data

(63) Continuation of application No. 17/257,816, filed as application No. PCT/US2019/040206 on Jul. 1, 2019, now Pat. No. 12,017,195.

(Continued)

(51) Int. Cl.
B01J 19/00 (2006.01)
C07K 1/04 (2006.01)

(52) U.S. Cl.
CPC ....... *B01J 19/0093* (2013.01); *B01J 19/0046* (2013.01); *C07K 1/045* (2013.01); *B01J 2219/00317* (2013.01); *B01J 2219/00529* (2013.01); *B01J 2219/00596* (2013.01); *B01J 2219/00653* (2013.01);

(Continued)

(58) Field of Classification Search
CPC ............... B01J 19/0046; B01J 19/0093; B01J 2219/00351; B01J 2219/00511; B01J 2219/00862; B01J 2219/00891; B01J 2219/00317; B01J 2219/00529; B01J 2219/00596; B01J 2219/00653; B01J 2219/00659; B01J 2219/00713; B01J 2219/00722; B01J 2219/00822;

(Continued)

(56) References Cited

U.S. PATENT DOCUMENTS

| | | | |
|---|---|---|---|
| 12,017,195 B2 | 6/2024 | Qing et al. | |
| 2013/0109596 A1* | 5/2013 | Peterson | ............ C12N 15/1093 506/40 |

(Continued)

OTHER PUBLICATIONS

Chow, B. Y. et al., "Photoelectrochemical synthesis of DNA microarrays", PNAS, Applied Physical Sciences, Sep. 8, 2009, pp. 15219-15224, vol. 106, No. 36, available at: https://www.pnas.org/content/pnas/106/36/15219.full.pdf, pp. 15219-15224.

(Continued)

*Primary Examiner* — Lessanework Seifu

(74) *Attorney, Agent, or Firm* — Womble Bond Dickinson (US) LLP

(57) ABSTRACT

The present disclosure provides an apparatus for synthesizing a biopolymer, a method for preparing an apparatus for synthesizing a biopolymer, and a method of synthesizing a biopolymer.

22 Claims, 21 Drawing Sheets

Related U.S. Application Data

(60) Provisional application No. 62/693,037, filed on Jul. 2, 2018.

(52) U.S. Cl.
CPC ................. *B01J 2219/00659* (2013.01); *B01J 2219/00713* (2013.01); *B01J 2219/00722* (2013.01); *B01J 2219/00822* (2013.01); *B01J 2219/00853* (2013.01); *B01J 2219/00855* (2013.01)

(58) Field of Classification Search
CPC .... B01J 2219/00853; B01J 2219/00855; B01J 2219/0099; C07K 1/045
See application file for complete search history.

(56) References Cited

U.S. PATENT DOCUMENTS

| | | |
|---|---|---|
| 2016/0186166 A1 | 6/2016 | Poehmerer et al. |
| 2016/0305905 A1 | 10/2016 | Hinz et al. |
| 2018/0280968 A1 | 10/2018 | Qing et al. |
| 2020/0187862 A1 | 6/2020 | Jiao et al. |
| 2021/0247347 A1 | 8/2021 | Lindsay et al. |

OTHER PUBLICATIONS

International Preliminary Report on Patentability dated Aug. 17, 2020, in International Patent Application No. PCT/US2019/040206, 14 pages.

International Search Report and Written Opinion of the International Searching Authority, mailed Sep. 30, 2019, corresponding to PCT/US2019/040206, 18 pages.

Mcdermott, M. L. et al., "DNA's Chiral Spine of Hydration", ACS Central Science, 2017, pp. 708-714, vol. 3, No. 7, American Chemical Society Publications.

U.S. Office Action from U.S. Appl. No. 17/257,816, dated Sep. 20, 2023, 10 pages.

* cited by examiner

FIG. 9A
FIG. 9B
FIG. 9C
FIG. 9D
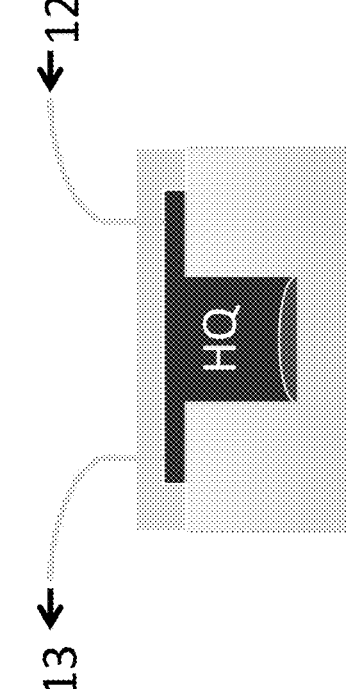
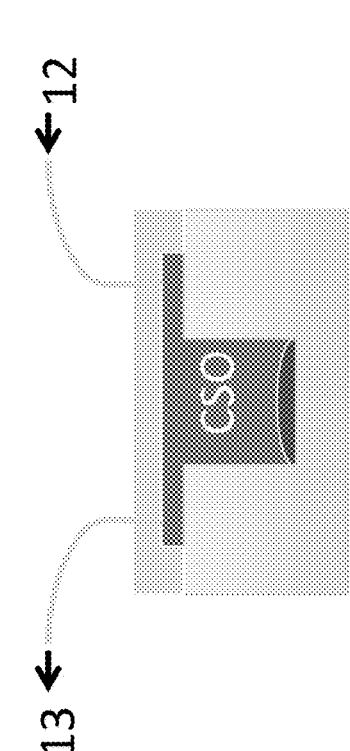

Exposure time:500ms/20x

APPARATUS AND METHODS FOR SYNTHESIZING BIOPOLYMERS

CROSS-REFERENCE TO RELATED APPLICATION(S)

The present application is a continuation of U.S. patent application Ser. No. 17/257,816, filed on Jan. 4, 2021, which is a U.S. national stage entry, under 35 U.S.C. § 371, of International Application Number PCT/US2019/040206, filed on Jul. 1, 2019, which claims priority to and the benefit of U.S. Provisional Application No. 62/693,037, filed on Jul. 2, 2018; the entire contents of all of the documents identified in this paragraph are incorporated herein by reference.

FEDERALLY SPONSORED RESEARCH OR DEVELOPMENT

This invention was made with government support under R21 HG009363 awarded by the National Institutes of Health and FA9550-16-1-0052 awarded by the Air Force Office of Scientific Research (AFOSR). The government has certain rights in the invention.

SUMMARY

The present disclosure provides an apparatus for synthesizing a biopolymer. The apparatus comprises (a) a substrate comprising a top surface and a plurality of wells, wherein each of the plurality of wells comprises a first electrode disposed on the bottom of the well and a linker attached to the sides of the well; and (b) a fluidic chamber system disposed on the top surface of the substrate.

The present disclosure also provides a method for preparing an apparatus. The method comprises (a) forming a plurality of wells on a substrate; (b) applying a first electrode to the bottom of the well; (c) attaching a linker to the sides of the well; and (d) affixing a fluidic chamber onto the substrate.

The present disclosure also provides a method of synthesizing an oligonucleotide. The method comprises (a) providing an apparatus as herein described; (b) introducing a solution comprising a first nucleotide phosphoramidite monomer into the well, wherein the first phosphoramidite monomer comprises a 5'-protecting group, an acid sensitive protecting group and optionally a base sensitive protecting group, and wherein the first phosphoramidite monomer reacts with the linker attached to the side walls of the well to form a linked nucleotide with a phosphite triester; (c) removing the solution from step (b) from the well; (d) introducing a solution comprising a capping reagent into the well, wherein the capping reagent reacts with any unreacted linker from step (b) to form a capped linker; (e) removing the solution from step (d) from the well; (f) introducing a solution comprising an oxidant into the well, wherein the oxidant converts the phosphite triester of the linked nucleoside to a phosphate triester; (g) removing the solution from step (f) from the well; (h) introducing a solution comprising a first redox reagent into the well, wherein a local potential is applied to the electrode inside the selected well such that the electrochemical reaction controlled by the potential induces the removal of 5'-protecting group; in one of the embodiment such electrochemical reaction involves the oxidation of hydroquinone which decreases pH locally inside the well; (i) removing the solution from step (h) from the well; (j) repeating steps (b) through (i) to synthesize a protected oligonucleotide; and (k) introducing a solution comprising a second deprotecting reagent into the well, wherein the second deprotecting agent removes the protecting groups on the oligonucleotide.

BRIEF DESCRIPTION OF THE FIGURES

FIG. 3A shows the application of a photo resist onto the surface of a substrate to define a well. FIG. 3B shows etching of the substrate to create a well having a defined depth. FIG. 3C shows the application of a first electrode to the bottom of the well. FIG. 3D shows the removal of the photo resist.

FIG. 4A shows the application of a passivation layer on a substrate. FIG. 4B shows the application of a photo resist onto the surface of a substrate to define a well. FIG. 4C shows etching of the substrate to create a well having a defined depth. FIG. 4D shows the application of a first electrode to the bottom of the well. FIG. 4E shows the removal of the photo resist.

FIG. 5A shows the application of a photo resist onto the surface of a substrate to seal all the trenches. FIG. 5B shows the exposure and post exposure baking proses to define the passivation layer.

FIG. 5C shows the development and removal of unexposed resist such that all metal surfaces except that in the reaction sites are sealed (in FIG. 5 the metal cross section represent the connection wires that is sealed by this passivation as in FIG. 2C, for all the other cases, the metal cross section represent the reaction sites that is exposed as in FIG. 2D).

FIG. 9A-FIG. 9H show a method of synthesizing oligonucleotides according to an embodiment of the disclosure. FIG. 9A shows the first step in which a phosphoramidite monomer is introduced into the well. The monomer reacts with the linker attached to the side walls of the wells to form a nucleoside with a phosphite triester linked to the side walls of the well. FIG. 9B shows the second step of capping in which unreacted linker is capped with an unreactive group. FIG. 9C shows the third step of oxidation in which the phosphite triester is converted to a phosphate triester. FIG. 9D shows the fourth step of electrochemically-controlled deprotection in which 5'-protecting group is removed. FIG. 9E shows the fifth step in which a second phosphoramidite monomer is introduced into the well. The second phosphoramidite monomer reacts with 5'-OH of the linked nucleotide to form a dinucleotide phosphite triester. FIG. 9F shows the sixth step of oxidation in which the phosphite triester is converted to a phosphate triester. FIG. 9G shows the seventh step of deprotection in which the protecting groups on from the bases and phosphates are removed. FIG. 9H shows the final step of deprotection in which the cyanoethyl groups from the nucleotide are removed

FIG. 18 A shows the fluorescent optical image of electrochemically activated reaction site. FIG. 18 B shows the fluorescent intensity measured from FIG. 18A. FIG. 18 C shows the fluorescent optical image of another electrochemically activated reaction site. FIG. 18 D shows the fluorescent intensity measured from FIG. 18 C.

DETAILED DESCRIPTION

Figures 1A, 1B, 1C:
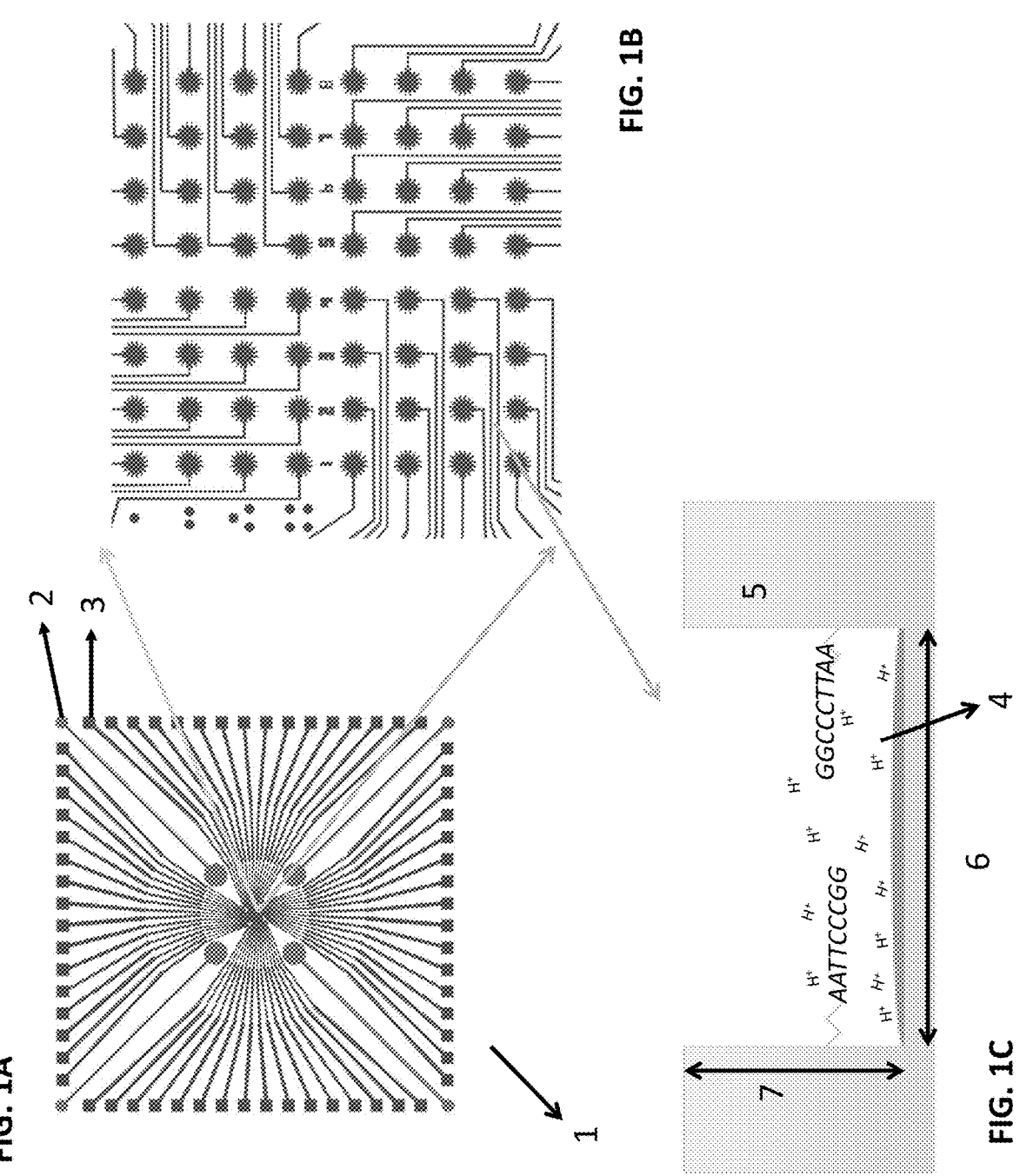
FIG. 1A shows the apparatus design according to a first embodiment of the disclosure.
FIG. 1B shows an exploded view of an array of individually addressable reaction sites connected to an external contact pad.
FIG. 1C shows a side view of the reaction site.

In various embodiments, the invention includes some or all of the following:

1. An apparatus for synthesizing a biopolymer, the apparatus comprising:
   (a) a substrate comprising a top surface and a plurality of wells, wherein each of the plurality of wells comprises a first electrode disposed on the bottom of the well and a linker attached to the sides of the well; and
   (b) a fluidic chamber system disposed on the top surface of the substrate.
2. The apparatus according to the above 1, wherein the distance between a first well and a second well is about 1 to about 200 μm.
3. The apparatus according to the above 1, wherein the diameter of the wells is about 1 to about 500 μm.
4. The apparatus according to the above 1, wherein the substrate is selected from glass, sputtered $SiO_2$, PECVD, $SiO_2$ and the like.
5. The apparatus according to the above 1, wherein the depth of the well is from about 500 nm to about 500 μm.
6. The apparatus according to the above 1, wherein the depth of the well is from about 500 nm to 10 μm.
7. The apparatus according to the above 1, wherein the first electrode comprises palladium, platinum, gold, or carbon.
8. The apparatus according to the above 1, wherein the linker comprises a hydroxy functionalized silane.
9. The apparatus according to the above 1, wherein the linker comprises an amine or thiol functionalized silane.
10. The apparatus according to the above 1, wherein the linker is (N-(3-triethoxysilylpropyl)-4-hydroxybutyramide.
11. The apparatus according to the above 1, wherein the fluidic chamber system comprises polydimethylsiloxane (PDMS).
12. The apparatus according to the above 1, wherein the fluid chamber system has a height of about 50 μm to 10 mm.
13. The apparatus according to the above 1, wherein the fluid chamber system comprising a second electrode.
14. The apparatus according to the above 13, wherein the second electrode comprises palladium, platinum, gold, or carbon.
15. The apparatus according to the above 1, wherein the fluid chamber system further comprises a system for introducing and removing liquids from the well.
16. A method for preparing an apparatus, comprising
   a. forming a plurality of wells on a substrate;
   b. applying a first electrode to the bottom of the well;
   c. passivating the surface of the connections of the electrodes;
   d. attaching a linker to the sides of the well; and
   e. affixing a fluidic chamber onto the substrate.
17. The method of the above 16, wherein step (a) comprises:
   i. applying a photo resist onto the surface of the substrate to define the plurality of wells; and
   ii, etching the substrate to create the plurality of wells.

18. The method of the above 16, wherein the substrate is selected from glass, sputtered SiO$_2$, PECVD, SiO$_2$ and the like.

19. The method of the above 16, wherein the first electrode comprises palladium, platinum, gold, or carbon.

20. The method of the above 16, wherein step (b) comprises depositing a metal selected from the group consisting of palladium, platinum, gold any other metals that is suitable for electrochemical control in the deprotection reagent;

21. The method of the above 17, wherein step (b) further comprises removing the photo resist.

22. The method of the above 16, wherein step (c) comprises immersing the substrate from step (b) into a linker solution for a period of time; and removing the linker solution.

23. The method of the above 16, wherein the fluid chamber system comprises a second electrode.

24. The method of the above 23, wherein the second electrode comprises palladium, platinum, gold, carbon or other conducting materials suitable for electrochemical control in the deprotection reagent.

25. The method of the above 16, wherein the fluid chamber system further comprises a system for introducing and removing liquids from the well.

26. A method of synthesizing an oligonucleotide, the method comprising (a) providing an apparatus according to any one of the above 1 to 15;

(b) introducing a solution comprising a first nucleoside phosphoramidite monomer into the well, wherein the first phosphoramidite monomer comprises a 5'-protecting group, an acid sensitive protecting group and optionally a base sensitive protecting group, and wherein the first phosphoramidite monomer reacts with the linker attached to the side walls of the well to form a linked nucleoside through a phosphite triester;

(c) removing the solution from step (b) from the well;

(d) introducing a solution comprising a capping reagent into the well, wherein the capping reagent reacts with any unreacted linker from step (b) to form a capped linker;

(e) removing the solution from step (d) from the well;

(f) introducing a solution comprising an oxidant into the well, wherein the oxidant converts the phosphite triester of the linked nucleoside to a phosphate triester;

(g) removing the solution from step (f) from the well;

(h) introducing a solution comprising a first deprotecting reagent into the well, wherein the deprotecting reagent is electrochemically activated and removes 5'-protecting group; in one embodiment, this activation involves the oxidation of hydroquinone to locally generate protons inside the well.

(i) removing the solution from step (h) from the well;

(j) repeating steps (b) through (i) to synthesize a protected oligonucleotide; and (k) introducing a solution comprising a second deprotecting reagent into the well, wherein the second deprotecting agent removes the protecting groups on the oligonucleotide.

27. The method of the above 26, wherein the capping reagent is acetic anhydride.

28. The method of the above 26, wherein the capped linker comprises an acetate group.

29. The method of the above 26, wherein the oxidant is (1S)-(+)-(10-camphorsulfonyl)-oxaziridine (CSO).

30. The method of the above 26, wherein the first deprotecting reagent removes a 5'-trityl group.

31. The method of the above 30, wherein the first deprotecting reagent is electrochemically generated acid.

32. The method of the above 26, wherein the second deprotecting reagent removes the phosphate protecting group.

33. The method of the above 26, wherein the second deprotecting reagent removes the acid sensitive protecting group.

34. The method of the above 31-33, wherein the second deprotecting reagent is ethylenediamine.

DEFINITIONS

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

Apparatus

The present disclosure provides an apparatus for synthesizing a biopolymer. The biopolymer is an oligonucleotide in one embodiment and a protein in a second embodiment. In one aspect, the biopolymer is DNA. In a second aspect, the biopolymer is RNA. In a third aspect, the biopolymer is a peptide.

The apparatus comprises (a) a substrate comprising a top surface and a plurality of wells, wherein each of the plurality of wells comprises a first electrode disposed on the bottom of the well and a linker attached to the sides of the well; and (b) a fluidic chamber system disposed on the top surface of the substrate.

In one embodiment, the distance between a first well and a second well is about 1 to about 200 μm. In another embodiment, the distance between a first well and a second well is about 1 to about 10 μm.

In one embodiment, the substrate is quartz. In other embodiments, the substrate is selected from glass, sputtered SiO$_2$, PECVD, SiO$_2$ and the like.

In one embodiment, the depth of the well is from about 500 nm to 500 μm. In another embodiment, the depth of the well is from about 500 nm to 10 μm.

In one embodiment, the first electrode comprises palladium. In another embodiment, the first electrode comprises a material selected from, but not limited to, gold, iridium, palladium, platinum or carbon.

In one embodiment, the linker comprises a hydroxy functionalized silane. In one aspect of this embodiment, the linker is (N-(3-triethoxysilylpropyl)-4-hydroxybutyramide. In another embodiment, the linker comprises an amino or thiol functionalized silane. In one aspect of this embodiment, the linker is (3-aminopropyl) triethoxysilane (APTES).

In one embodiment, the fluidic chamber system comprises polydimethylsiloxane (PDMS). In another embodiment, the fluidic chamber system comprises PTFE. In another embodiment, the fluidic chamber system comprises parylene-C.

In one embodiment, the fluid chamber system has a height from about 50 μm to about 10 mm. In another embodiment, the fluid chamber system has a height from about 100 μm to about 5 mm. In another embodiment, the fluid chamber system has a height from about 500 μm to about 2.5 mm. In another embodiment, the fluid chamber system has a height from about 900 μm to about 2.0 mm.

In one embodiment, the fluid chamber system comprising a second electrode. In one aspect of this embodiment, the second electrode is palladium. In another embodiment, the second electrode comprises a material selected from gold, iridium, palladium, platinum or carbon.

In one embodiment, the fluid chamber system further comprises a system for introducing and removing liquids from the well.

FIG. 1A shows an apparatus design according to an embodiment of the disclosure. The apparatus 1 comprises 4 counter electrodes 2 away from the reaction sites and 64 individually controlled electrodes 3. represents an integrated working electrode. FIG. 1B shows an array of individually addressable reaction sites connected to an external pad. FIG. 1C shows an exploded view of the reaction sites in which 4 is an electrode, 5 is the substrate, 6 is the distance between reaction sites and 7 is the depth of the reaction site. The DNA sequence is synthesized on the functionalized side wall of reaction site.

The distance 6 between reaction sites are limited only by the diffusion length of proton. The distance 6 is from about 1 μm to about 100 μm. In some embodiments, the distance 6 is from about 30 μm to about 70 μm.

Figures 2A, 2B, 2C, 2D:
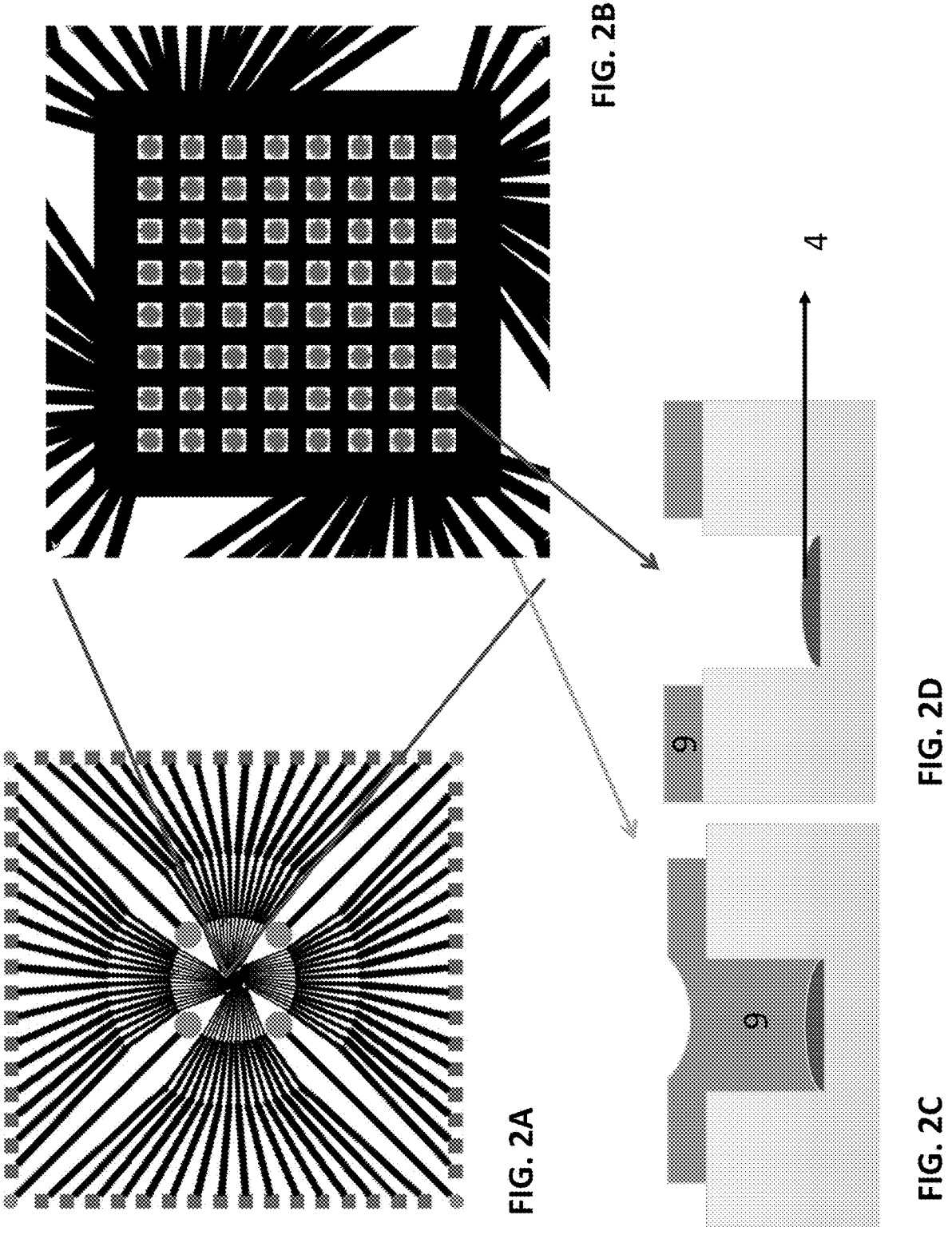
FIG. 2A shows the apparatus design according to a second embodiment of the disclosure in which the top surface of the apparatus, excluding the reaction sites (wells), comprises a passivation layer.
FIG. 2B shows an exploded view of an array of individually addressable reaction sites connected to an external contact pad.
FIG. 2C shows a side view of the reaction site after application of a passivation layer.
FIG. 2D shows a side view of the reaction site in which the top surface of the apparatus, excluding the reaction sites, comprises a passivation layer.

FIG. 2A-FIG. 2B show an apparatus design according to a second embodiment of the disclosure. This apparatus is configured so that only the reactions sites are exposed, the effect of which is to minimize unwanted reactions. As shown in FIG. 2C, a photo resist 9 is initially applied to the substrate 5 and into the well, covering the first electrode 4. At reaction sites, the photo resist 9 is removed from the well, exposing the first electrode 4 (FIG. 2D).

Method of Preparing Apparatus

The present disclosure also provides a method for preparing an apparatus. The method comprises (a) forming a plurality of wells on a substrate; (b) applying a first electrode to the bottom of the well; (c) attaching a linker to the sides of the well; and (d) affixing a fluidic chamber onto the substrate.

In one embodiment, step (a) comprises: (i) applying a photo resist onto the surface of the substrate to define the plurality of wells; and (ii) etching the substrate to create the plurality of wells.

In one embodiment, the substrate is silicon dioxide, quartz is used in one of the apparatus. In another embodiment, the substrate is selected from glass, sputtered SiO$_2$, PECVD, SiO$_2$ and the like.

In one embodiment, the first electrode is palladium. In another embodiment, the first electrode comprises a material selected from, but not limited to, gold, iridium, palladium, platinum or carbon.

In one embodiment, step (b) comprises thermally evaporating palladium. In another embodiment, step (b) comprises a material selected from gold, iridium, palladium, platinum or carbon.

In one embodiment, step (b) further comprises removing the photo resist.

In one embodiment, step (c) comprises immersing the substrate from step (b) into a linker solution for a period of time; and removing the linker solution. In some aspects of this embodiment, step (c) comprises baking at about 100 to about 150° C. for about 0.1 hr to about 2 hr.

In one embodiment, the fluid chamber system comprises a second electrode.

In one embodiment, the second electrode is palladium. In another embodiment, the second electrode comprises a material selected from, but not limited to, gold, iridium, palladium, platinum or carbon.

In one embodiment, the fluid chamber system further comprises a system for introducing and removing liquids from the well.

Figure 3A:
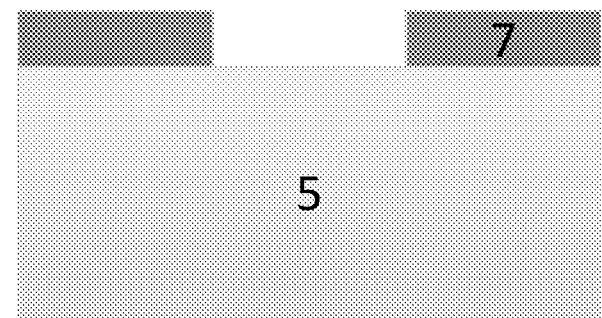
FIG. 3A-FIG. 3D show a method of preparing an apparatus according to a first embodiment of the disclosure.
Figure 3B:
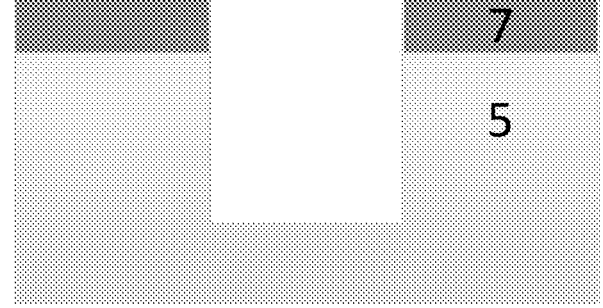
Figure 3C:
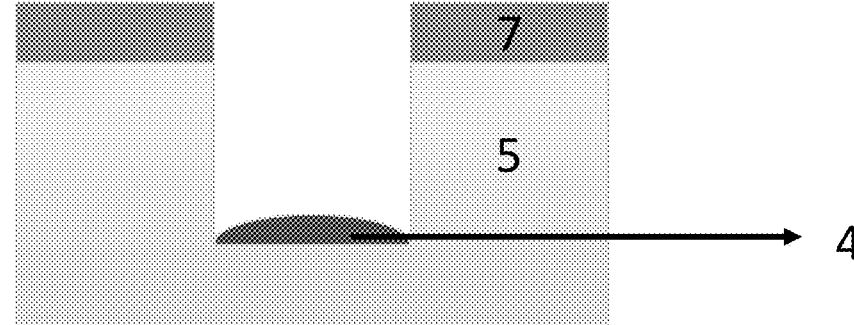
Figure 3D:
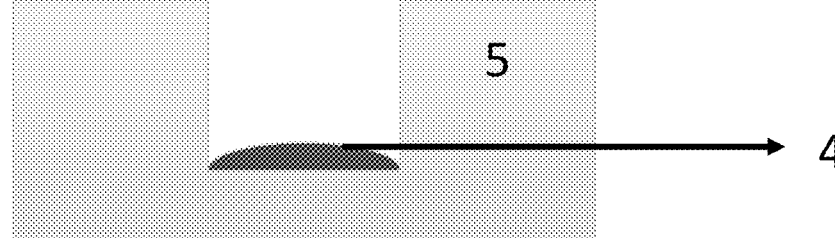

FIG. 3A-FIG. 3D show a first method of preparing an apparatus as described herein. In FIG. 3A, a photo resist 7 is applied onto the surface of a substrate 5 to define a well. The substrate 5 is etched to create a well having a defined depth (FIG. 3B). A first electrode 4 is applied to the bottom well, as shown in FIG. 3C. The photo resist 7 is then removed, as shown in FIG. 3D.

Figures 4A, 4B, 4C, 4D, 4E:
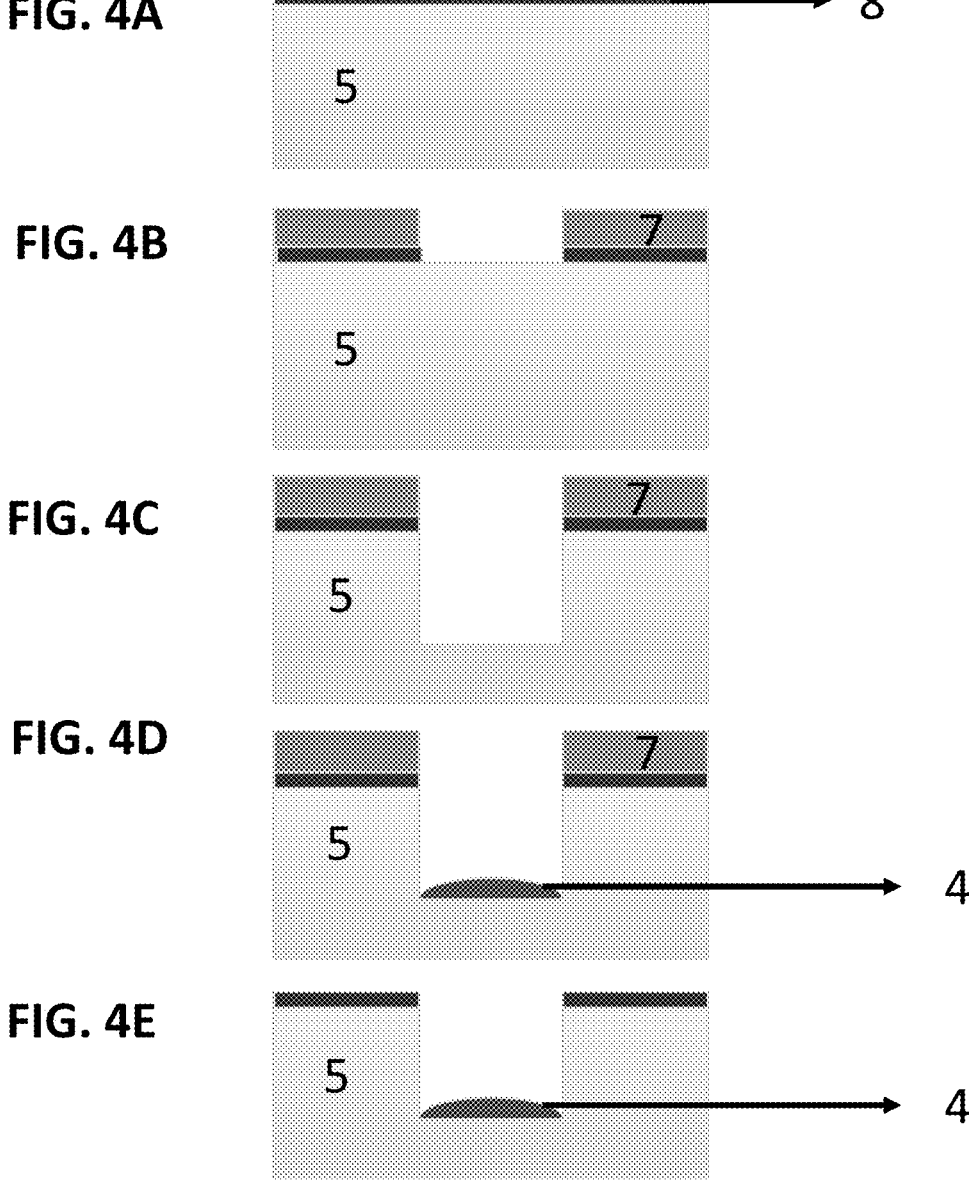
FIG. 4A-FIG. 4E show a method of preparing an apparatus according to a second embodiment of the disclosure.

FIG. 4A-FIG. 4E show a method of preparing an apparatus according to a second embodiment of the disclosure. A Cr passivation layer 8 is thermally evaporated on a piranha cleaned quartz substrate 5 (FIG. 4A). A photo resist is spin coated and exposed to define a well (FIG. 4B). Cr is removed by Cr etchant. RIE etching is used to create a well structure with a defined depth (FIG. 4C). A palladium electrode is thermally evaporated onto the bottom of the well (FIG. 4D). Then, the photo resist is removed, as shown in FIG. 4E.

Figures 5A, 5B, 5C:
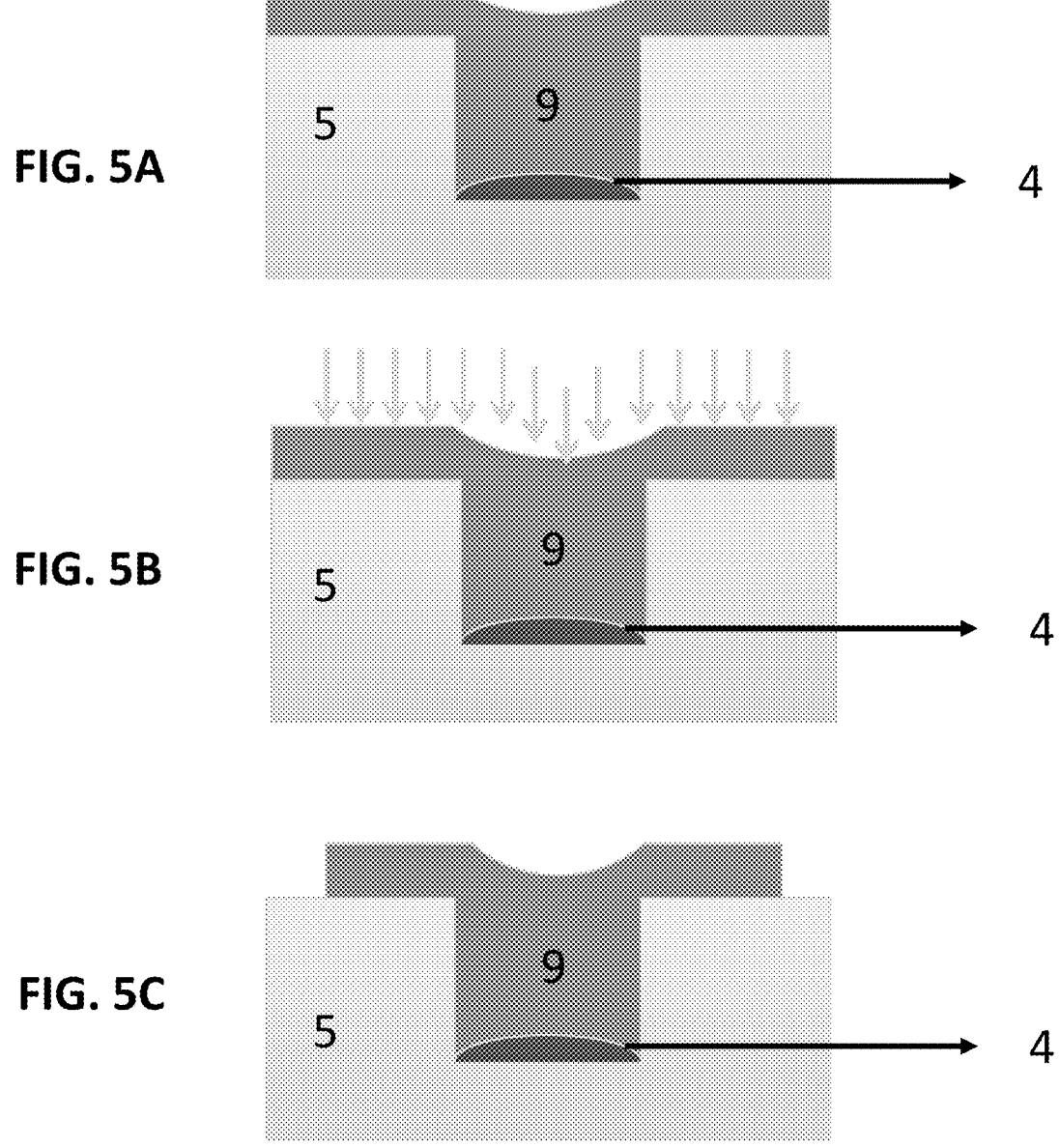
FIG. 5A-FIG. 5C shows the fabrication process of passivation layer according to an embodiment of the disclosure.

FIG. 5A-5C show a method of preparing an apparatus according to a third embodiment of the disclosure. As shown in FIG. 5A, a photo resist 9, such as SU-8 2002, is spin coated to the substrate 5 and into the trenches covering the first electrode 4. The photo resist passivation layer pattern is exposed and post-baked before development to yield a passivation layer that seals all trenches with metal connections (FIG. 5B), except for the reaction cite areas as marked in FIG. 2D. The passivation layer is finalized by a hard-baking procedure (FIG. 5C).

Figure 6:
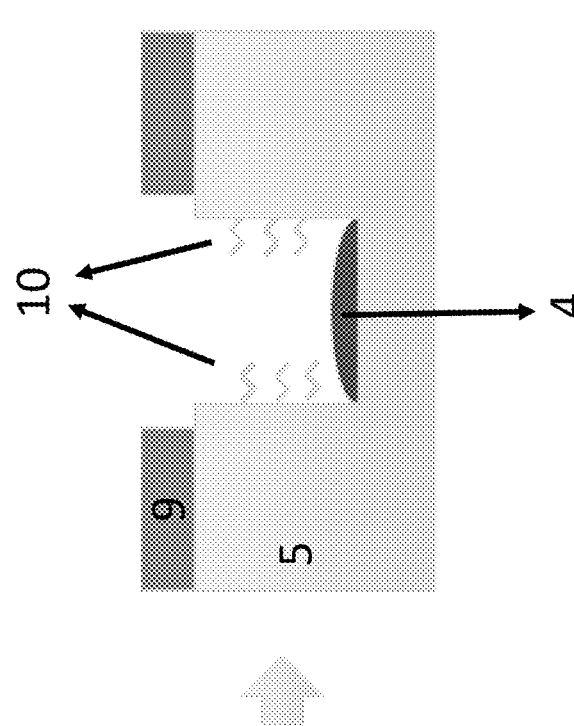
FIG. 6 shows the attachment of a linker to the sides of the well according to an embodiment of the disclosure.
Figure 6:
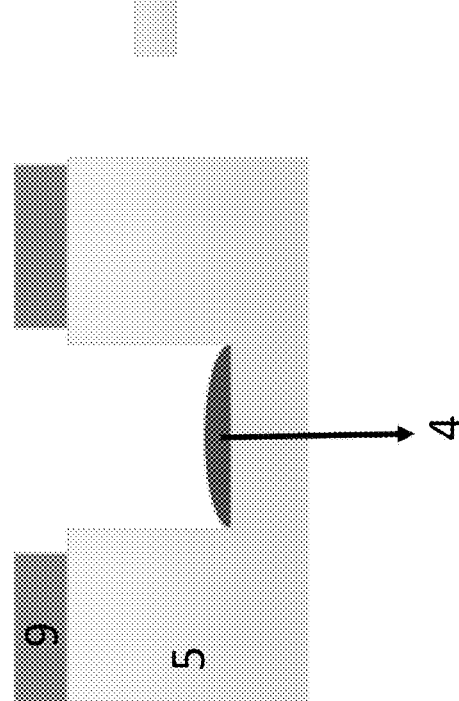

FIG. 6 shows the method for functionalizing the substrate with a linker 10. The apparatus is initially cleaned with UV/ozone. The apparatus is then immersed in a solution comprising the linker 10. In the immersion step, the linker 10 attaches to the sides of the wells. In one embodiment, the linker solution comprises linker, water and ethanol. In one embodiment, the linker is N-(3-triethoxysilylpropyl)-4-hydroxybutyramide. After immersion in the linker solution, the apparatus is baked, e.g., at about 120° C. for about 20 min.

Figure 7:
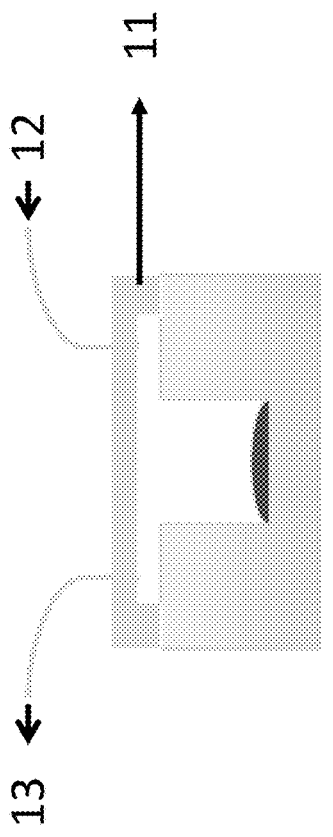
FIG. 7 shows an apparatus according to a third embodiment of the disclosure.
Figure 8:
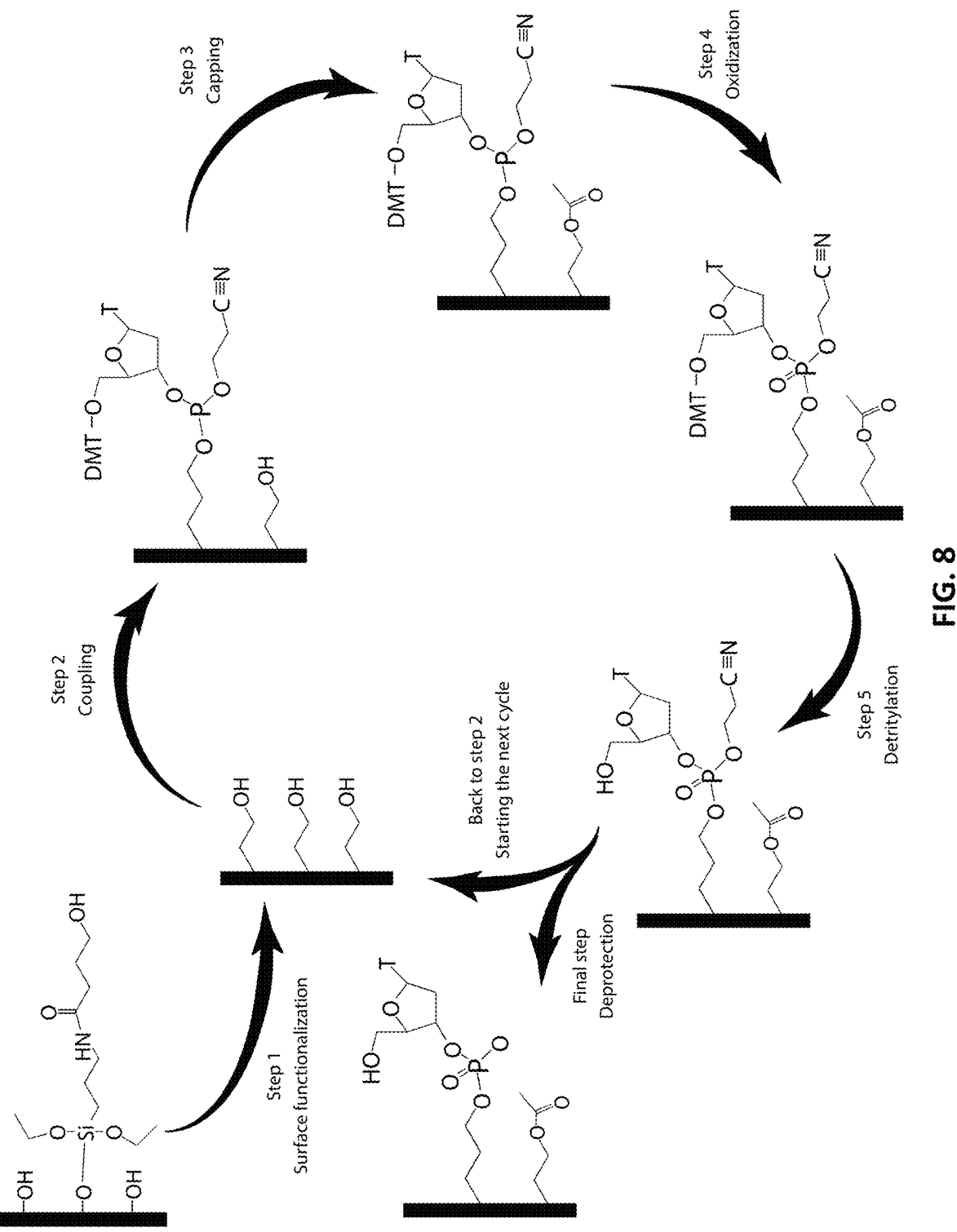
FIG. 8 shows a summary of the oligonucleotide synthesis cycle.

After the linker is attached to the sides of the wells, the apparatus is modified to contain a fluidic chamber system. As shown in FIG. 7, a PDMS chamber 11 is fixed onto the apparatus surface. Then, chemical inlet tubing 12 and outlet tubing 13 is fixed to the chamber. All chemicals are delivered into the chamber through a fluidic multiplexer Methods of Use The present disclosure also provides a method of synthesizing oligonucleotides. The method comprises (a) providing an apparatus as herein described; (b) introducing a solution comprising a first nucleoside phosphoramidite monomer and an activator into the well, wherein the first phosphoramidite monomer comprises a 5'-protecting group, an acid sensitive protecting group and optionally a base sensitive protecting group, and wherein the first phosphoramidite monomer reacts with the linker attached to the side walls of the well to form a linked nucleoside through a phosphite triester; (c) removing the solution from step (b) from the well; (d) introducing a solution comprising a capping reagent into the well, wherein the capping reagent reacts with any unreacted linker from step (b) to form a capped linker; (e) removing the solution from step (d) from the well; (f) introducing a solution comprising an oxidant into the well, wherein the oxidant converts the phosphite triester of the linked nucleoside to a phosphate triester; (g) removing the solution from step (f) from the well; (h) introducing a solution comprising a first deprotecting reagent into the well, wherein the deprotecting reagent removes 5'-protecting group; (i) removing the solution from step (h) from the well; (j) repeating steps (b) through (i) to synthesize a protected oligonucleotide; and (k) introducing a solution comprising a second deprotecting reagent into the well, wherein the second deprotecting agent removes the protecting groups on the oligonucleotide.

In one embodiment, the activator is 4,5-Dicyanoimidazole (DCI).

In one embodiment, the capping reagent is acetic anhydride. In one embodiment, the capping solution comprises acetic anhydride, dimethylaminopyridine, 2,6-lutidine and THF.

In one embodiment, the capped linker comprises an acetate group.

In one embodiment, oxidant is (1S)-(+)-(10-camphorsulfonyl)-oxaziridine (CSO). In one embodiment the oxidant solution comprises CSO and acetonitrile.

In one embodiment, the first deprotecting reagent electrochemically removes a 5'-trityl group. In one embodiment, the first deprotecting reagent is electrochemically generated acid. In one aspect of this embodiment, the localization of the pH change by electrochemical reaction is controlled by the depth and dimension of the reaction sites, the composition of the pH buffer solution above the reaction sites, and the duration of the electric bias applied at the electrodes. In one aspect, the pH buffer contains proton quencher 2,6 lutidine.

In one embodiment, the first deprotecting reagent is hydroquinone and 2-6 lutidine. In one embodiment, the first deprotecting reagent solution comprises hydroquinone, anthraquinone, tetraethylammonium p-toluene sulfonate and acetonitrile. In one embodiment, when the first deprotecting reagent solution is introduced, a potential is applied to the working electrode. In one embodiment, the potential is from about 1V to about 5V. In another embodiment, the potential is from about 2V to about 4V.

In another embodiment, the first deprotecting reagent is dichloroacetic acid. In one embodiment, the first deprotecting reagent solution comprises dichloroacetic acid in dichloromethane.

In one embodiment, the second deprotecting reagent removes the phosphate protecting group.

In one embodiment, the second deprotecting reagent removes the nucleobase protecting groups.

In one embodiment, the second deprotecting reagent is ethylenediamine. In one embodiment, the second deprotecting reagent solution comprises ethylenediamine and ethanol.

Figures 9E, 9F, 9G, 9H:
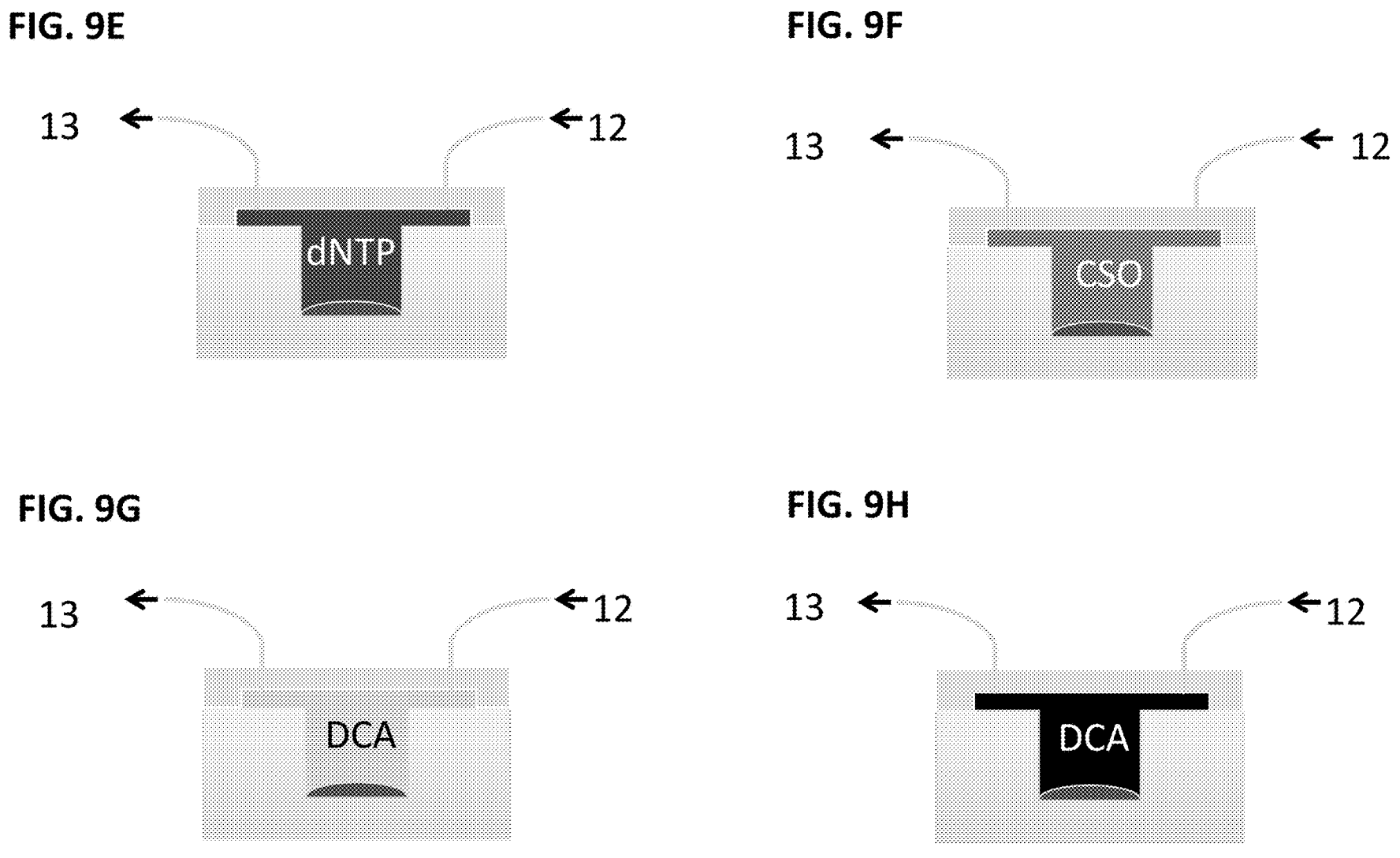

As shown in FIG. 8 and FIGS. 9A-9H, the linker attached to the side wells is functionalized by immersing the device into linker solution for about 5 minutes to about 180 minutes and then baking for about 1 min to about 180 minutes. In the second step, a solution comprising a first nucleoside phosphoramidite monomer and an activator are introduced into the well (FIG. 9A). The solution is flowed into the well from about 1 sec to about 15 min at a volume from about 1 μL to about 5 mL. In preferred embodiment, the solution is flowed into the well from about 1 sec to 1 min. In another preferred embodiment, the solution is flowed into the well for about 30 sec.

The solution from the second step is removed and then, in the third step, a solution comprising a capping reagent is introduced into the well (FIG. 9B). The solution is flowed into the well from about 1 sec to about 15 min at a volume from about 1 μL to about 5 mL. In preferred embodiment, the solution is flowed into the well from about 1 sec to 1 min. In another preferred embodiment, the solution is flowed into the well for about 15 sec. The capping reagent reacts with any unreacted linker from the second step to form a capped linker. The solution comprising the capping reagent is removed from the well.

In the fourth step, a solution comprising an oxidant is introduced into the well (FIG. 9C). The solution is flowed into the well from about 1 sec to about 15 min at a volume from about 1 μL to about 5 mL. In preferred embodiment, the solution is flowed into the well from about 1 sec to 5 min. In another preferred embodiment, the solution is flowed into the well for about 3 min. The oxidant converts the phosphite triester of the linked nucleoside to a phosphate trimester. The oxidant solution is then removed from the well.

A solution comprising a first deprotecting reagent is introduced into the well in the fifth step (FIG. 9D). The solution is flowed into the well from about 1 sec to about 20 min at a volume from about 1 μL to about 5 mL with a potential applied to the working electrode. In preferred embodiment, the solution is flowed into the well from about 1 sec to 5 min. In another preferred embodiment, the solution is flowed into the well for about 3 min. The deprotecting reagent removes 5'-protecting group. The deprotection reagent solution is removed and steps 1 through step 5 can be repeated a plurality of times as desired (FIG. 9E-FIG. 9G).

In the sixth step, a solution comprising a second deprotecting reagent is introduced into the well (FIG. 9H). The second deprotecting agent removes the protecting groups on the oligonucleotide. The solution is flowed into the well from about 1 sec to about 20 min at a volume from about 1 μL to about 5 mL. In preferred embodiment, the solution is flowed into the well from about 5 min to 15 min. In another preferred embodiment, the solution is flowed into the well for about 10 min.

In order that this invention be more fully understood, the following examples are set forth. These examples are for the purpose of illustration only and are not to be construed as limiting the scope of the invention in any way.

EXAMPLES

Example 1

Figure 10A:
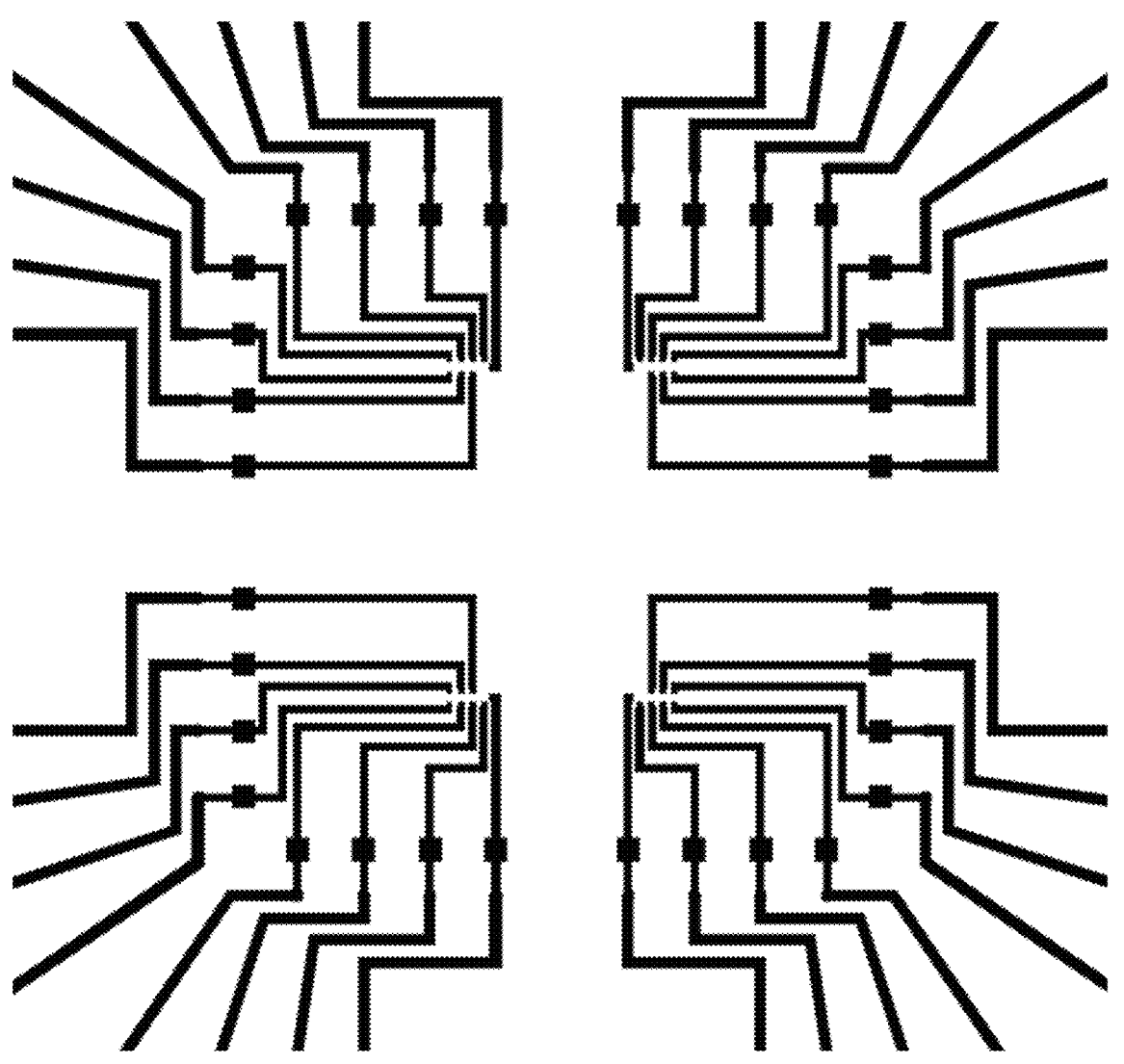
FIG. 10A shows an apparatus according to an embodiment of the disclosure and used in Example 1.

The objective of Example 1 was to demonstrate the ability of control DNA synthesis electrochemically. The apparatus used in Example 1 is shown in FIG. 10A. Palladium electrodes are deposit on quartz surface through electron-beam evaporation.

A two-cycle DNA synthesis was conducted in three main steps. In step 1, a dT-CE Phosphoramidite was attached to the functionalized silicon dioxide surface. In step 2, a 3.6V electric potential was applied to selected electrodes for 90 second to oxidize hydroquinone and the electrochemically generated proton deprotected the first nucleotide on the silicon dioxide surface. In step 3, a fluorescein labeled dT-CE phosphoramidite was coupled to the deprotected first nucleotide.

One positive control device and one negative control device were tested to compare the results. All three apparatuses were fabricated and tested under same controlled condition.

To evaluate the nonspecific binding of the fluorescent labeled nucleotide, during the detritylation step, the negative control device was flowed with hydroquinone deprotection solution for 10 minutes without electric activation. A 4 mW/488 nm laser was used for epi-fluorescence imaging light source.

To have a successful 2 cycle synthesis result to compare with, a positive control test was taken. During the detritylation step, a standard chemical deprotection (dichloroacetic acid deprotection solution) was performed.

Figure 10B:
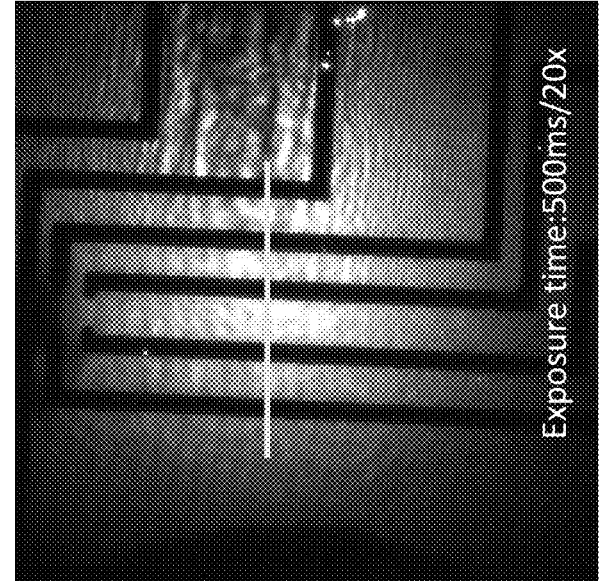
FIG. 10B shows the epifluorescence image of negative control test.
Figure 10C:
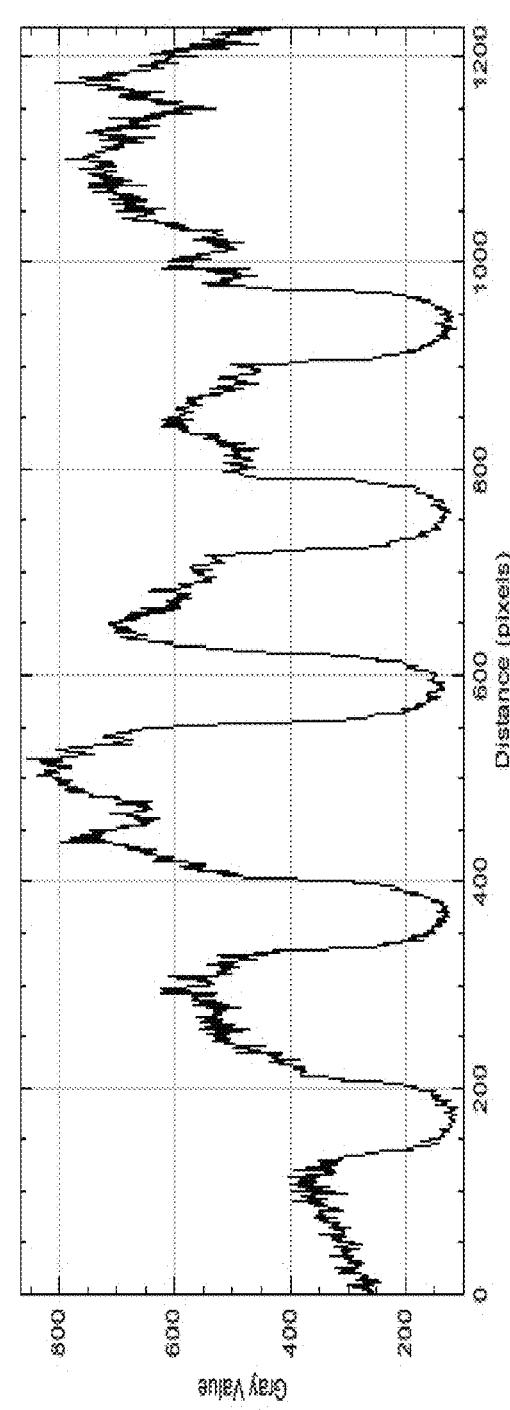
FIG. 10C shows the fluorescent intensity measured from FIG. 10B, indicating the background fluorescent intensity.
Figures 11A, 11B:
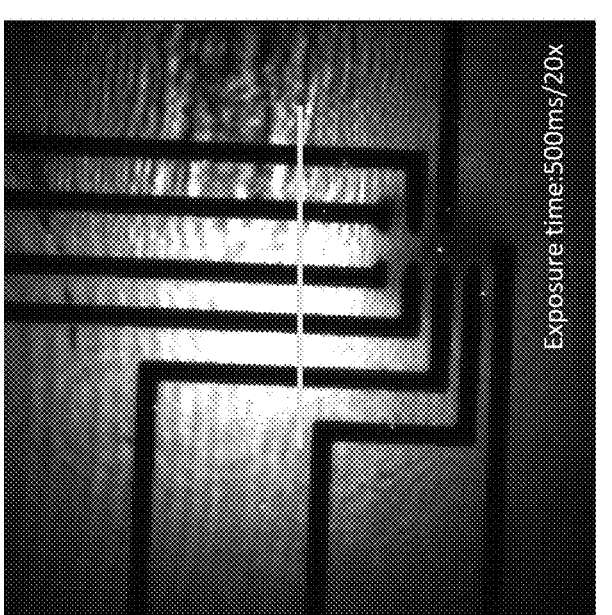
FIG. 11A shows the epifluorescence image of positive control test.
FIG. 11B shows the fluorescent intensity measured from FIG. 11A, indicating the fluorescent intensity of the positive control test.

Based on the synthesis result of the negative control, the fluorescent intensity measured (FIG. 10B) is no more than 800 (arbitrary unit). As for the synthesis result of the positive control, the fluorescent intensity measured (FIG. 11B) is about 4500. Taking the nonspecific binding fluorescent signal as noise, the signal/noise ratio of the positive control is around 5.6.

Figure 12A:
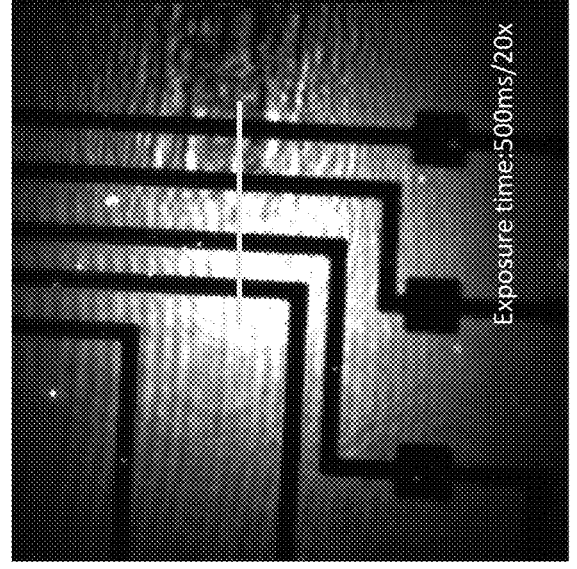
FIG. 12A shows the epifluorescence image of electrochemical deprotection result near activated electrode
Figure 12B:
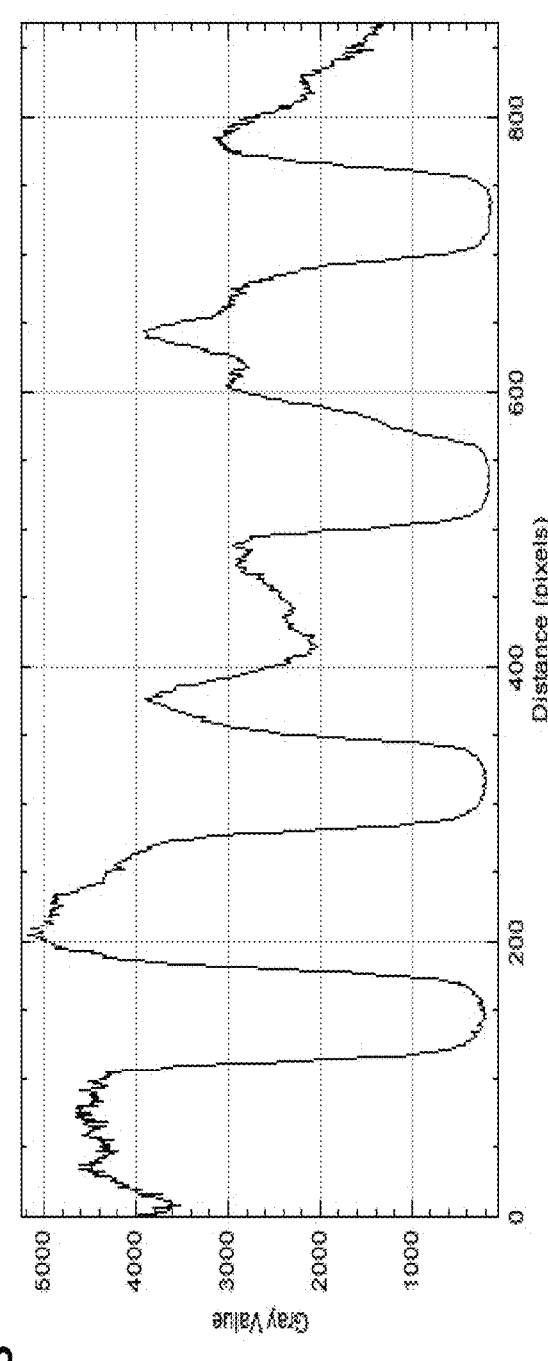
FIG. 12B shows the fluorescent intensity measured from FIG. 12A, indicating the fluorescent signal is comparable to positive control test.

The synthesis result from the electrochemical deprotection sample is shown in FIG. 12A. The fluorescent intensity measured (FIG. 12B) is around 4000 and the signal/noise ratio calculated is around 5, which is comparable to positive control.

These results show the successful demonstration of the ability to conduct DNA synthesis with electrochemical control. The yield/intensity of the apparatus was comparable with standard chemical controlled synthesis.

Example 2

Figure 13:
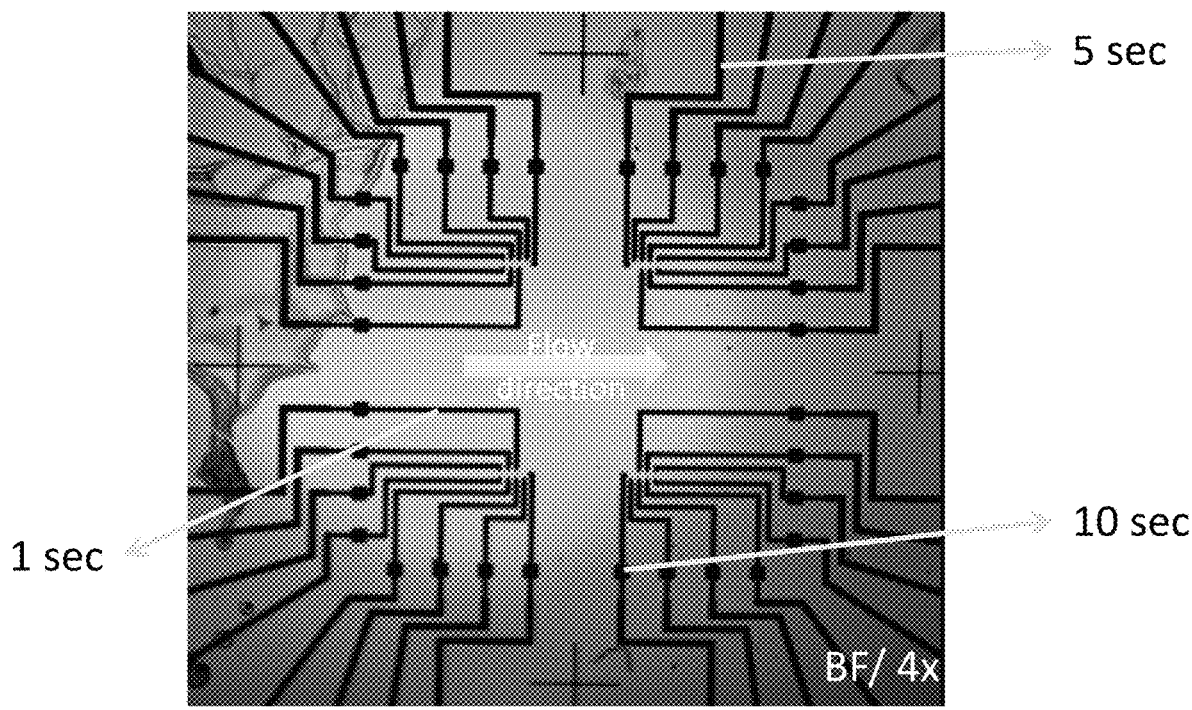
FIG. 13 shows an apparatus according to an embodiment of the disclosure and used in Example 2.

The objective of Example 2 was to demonstrate the ability to conduct localized electrochemical control of DNA synthesis and the diffusion control of electrochemically generated proton in the apparatus. The apparatus used in Example 2 is shown in FIG. 13. Palladium electrodes are deposit on quartz surface through electron-beam evaporation.

A two-cycle DNA synthesis was conducted in three main steps. In step 1, a dT-CE phosphoramidite was attached to the functionalized silicon dioxide surface. In step 2, an electric potential was applied to selected electrodes to oxidize hydroquinone and the electrochemically generated proton deprotected the first nucleotide on the silicon dioxide surface. Three activation time were selected: 1 second, 5 second, and 10 second. In step 3, a fluorescein labeled dT-CE Phosphoramidite was coupled to the deprotected first nucleotide.

Figure 14A:
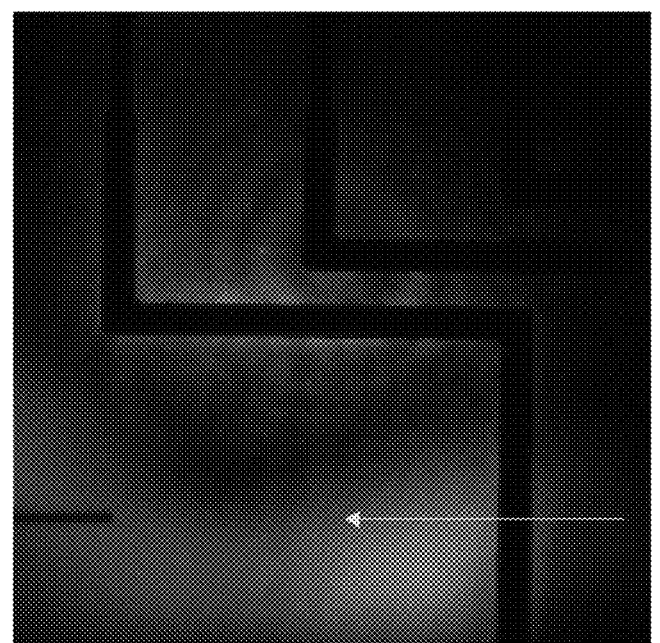
FIG. 14A shows the epifluorescent image of electrode that is activated for 1 second.
Figure 14B:
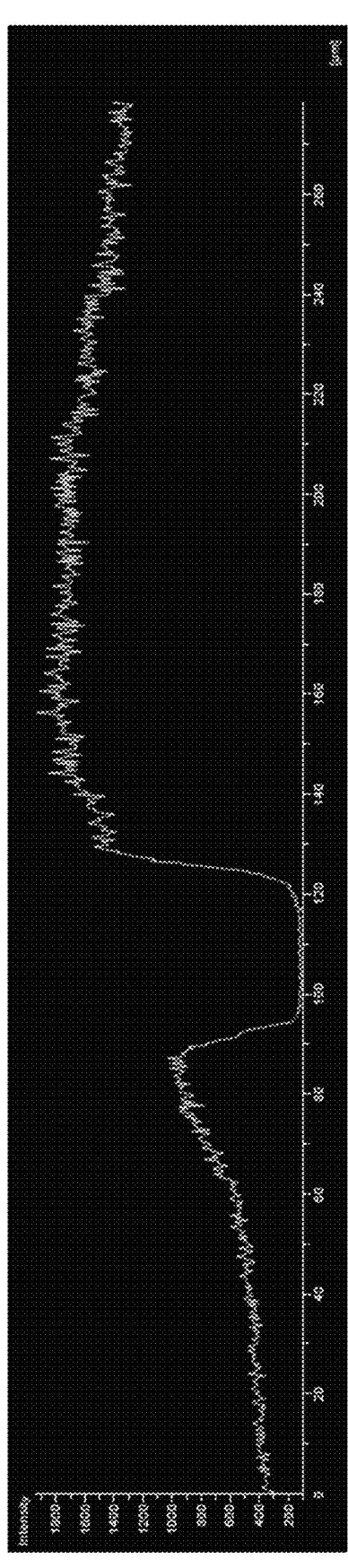
FIG. 14B shows the fluorescent intensity measured from FIG. 14A. The relatively low intensity indicates insufficient proton concentrating.
Figures 15A, 15B:
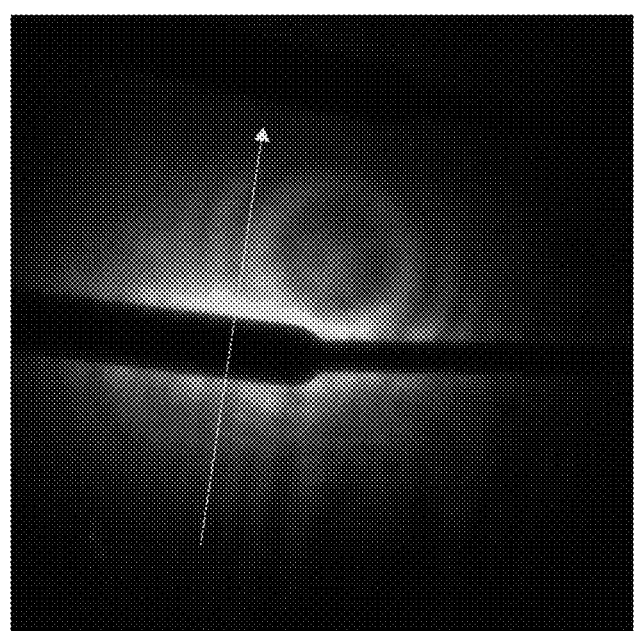
FIG. 15A shows the epifluorescent image of electrode that is activated for 5 second.
FIG. 15B shows the fluorescent intensity measured from FIG. 15A. The fluorescent intensity gradient indicates the diffusion of the electrochemically-generated proton.
Figures 16A, 16B:
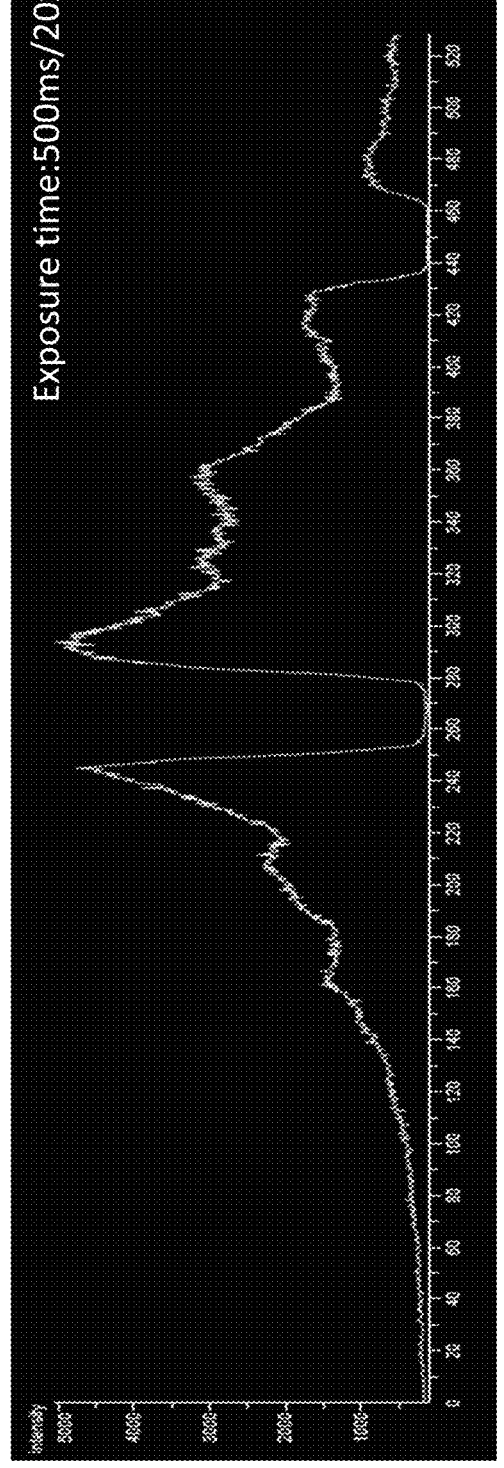
FIG. 16A shows the epifluorescent image of electrode that is activated for 10 second.
FIG. 16B shows the fluorescent intensity measured from FIG. 16A. The globally lighten up image indicates electrochemically generated proton may diffuse to inactivated area following the flowing direction of the reagents.

By the fact that fluorescent signal comes the second fluorescein labeled nucleotide, the fluorescent intensity was used as an indicator of the accessibility to electrical generated proton of the first nucleotide. The synthesis result shows a proportional increase of fluorescent intensity with electrode activation time. When the electrode is activated for 1 second (FIG. 14A), the highest fluorescent intensity around the trench is around 1800 (arbitrary unit) (FIG. 14B); for 5-second activation electrode (FIG. 15A), the fluorescent intensity is around 3500 (FIG. 15B); as for 10-second activation electrode (FIG. 16A), the fluorescent intensity is around 5000 (FIG. 16B). The synthesis result also indicates the proton diffusion length (the distance for the highest fluorescent intensity decades to background). For 1 second activation, the longest distance the electrochemical generated proton can travel is around 100 μm; for 5 second activation, the proton diffusion length is around 180 μm; and for 10 second activation, the proton diffusion length is around 240 μm. These analyses confirmed that the apparatus conducts a localized DNA synthesis. Also, with longer activation time, more proton is generated and hence introduced a higher synthesis yield (fluorescent intensity), but also allowed longer distance for proton to diffuse thus the deprotection was less localized. By adding 2,6 lutidine as a proton quencher, the proton generated around the electrode is neutralized by basic lutidine and hence reduce the proton diffuse distance.

Example 3

In this Example, a 12 mer DNA was synthesized through 12 sec electrochemical activation. The sequence was verified by hybridization with a fluorescent labeled complimentary DNA. Only the DNA with correct sequence shall hybridize with the fluorescent target and emit fluorescent signal. The result was compared with the hybridization of an identical sequence synthesized through conventional chemical activation.

The device comprises a chromium passivation top surface, 1 μm SiO₂ wells etched by RIE, and 100 nm palladium electrodes deposit at the bottom of the wells.

The SiO₂ surface was cleaned by 3 min BHF etching before linker functionalization for improved surface quality.

Figure 17:
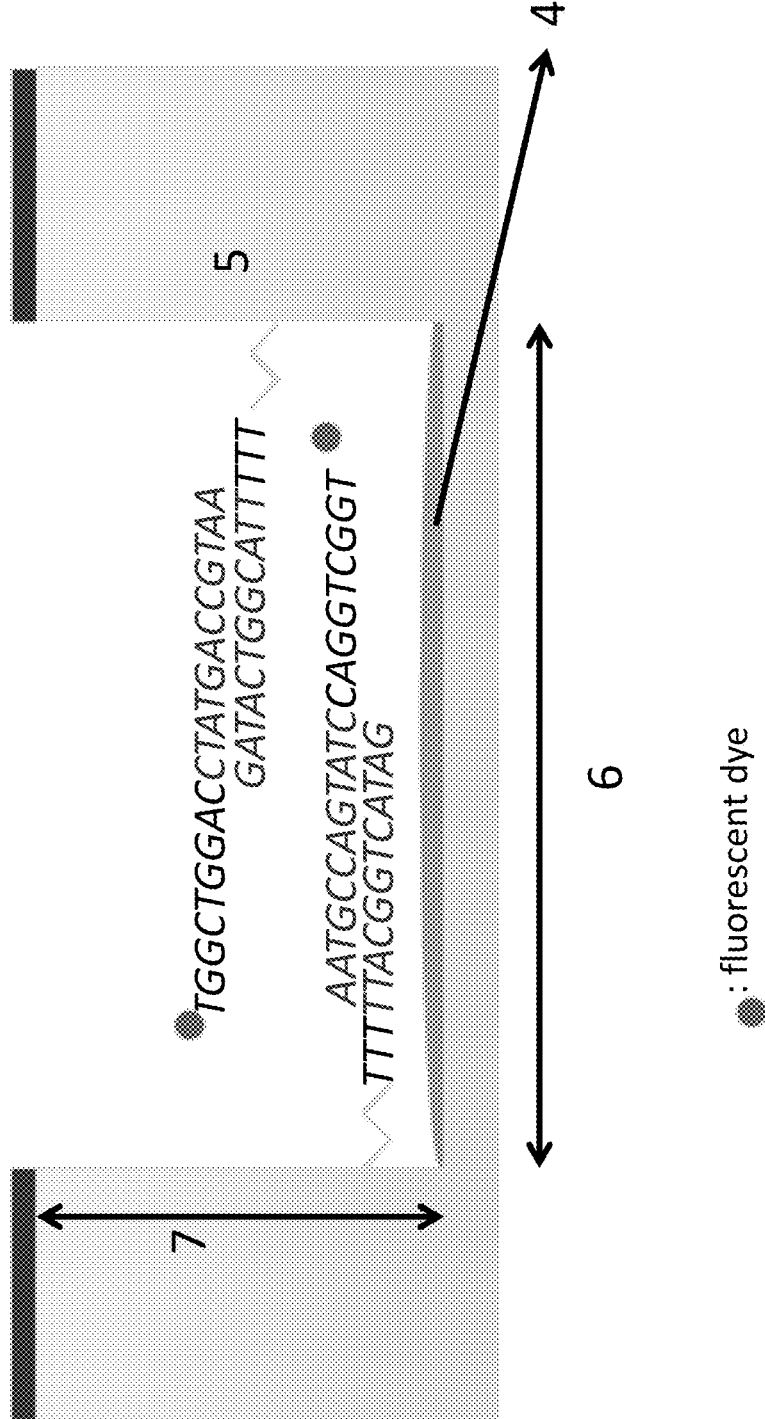
FIG. 17 shows a schematic diagram of a 12 mer DNA synthesis verified by hybridization with a fluorescent labeled complimentary DNA.

A 12 mer DNA (3'-TTT (spacer) TTA CGG TCA TAG GTC-5') was synthesized through 12 sec electrochemical activation. The purchased fluorescent labeled DNA target (5'-AAT GCC AGT ATC CAG GTC GG/3FluorT/-3') is complimentary to the 12 mer DNA synthesized. FIG. 17 illustrates the successful hybridization between synthesized DNA and fluorescent labeled complimentary target.

Figures 18A, 18B, 18C, 18D:
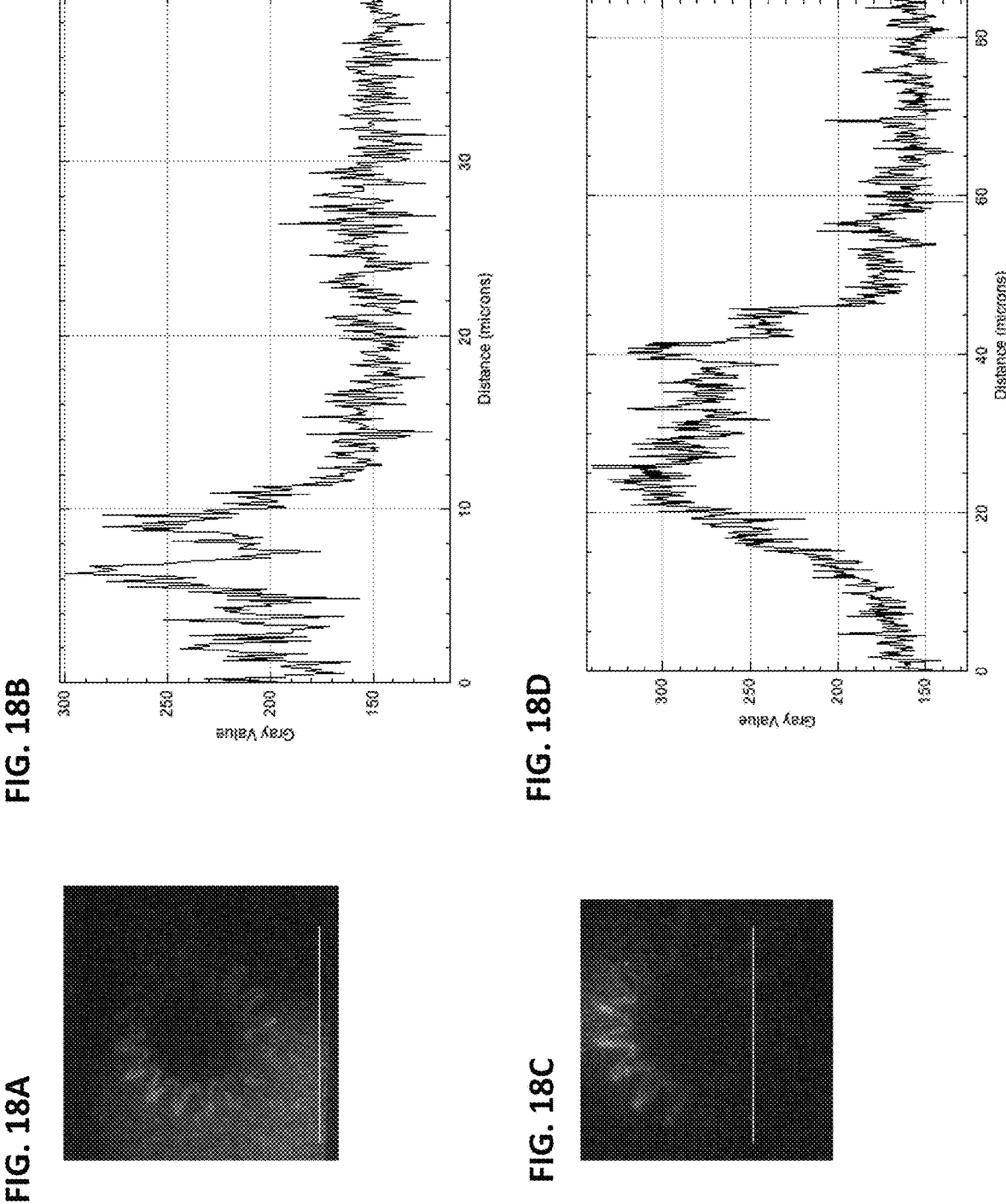
FIGS. 18A-18D show the results of the localized electrochemical synthesis of 12 mer DNA within the side walls of the reaction sites verified by hybridization with a fluorescent labeled complimentary DNA.
Figure 19A:
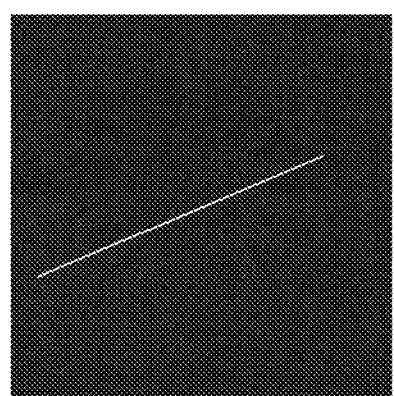
FIG. 19A and FIG. 19B show the results of negative control indicating that no obvious fluorescence is observed. The background intensity is 160.
Figure 19B:
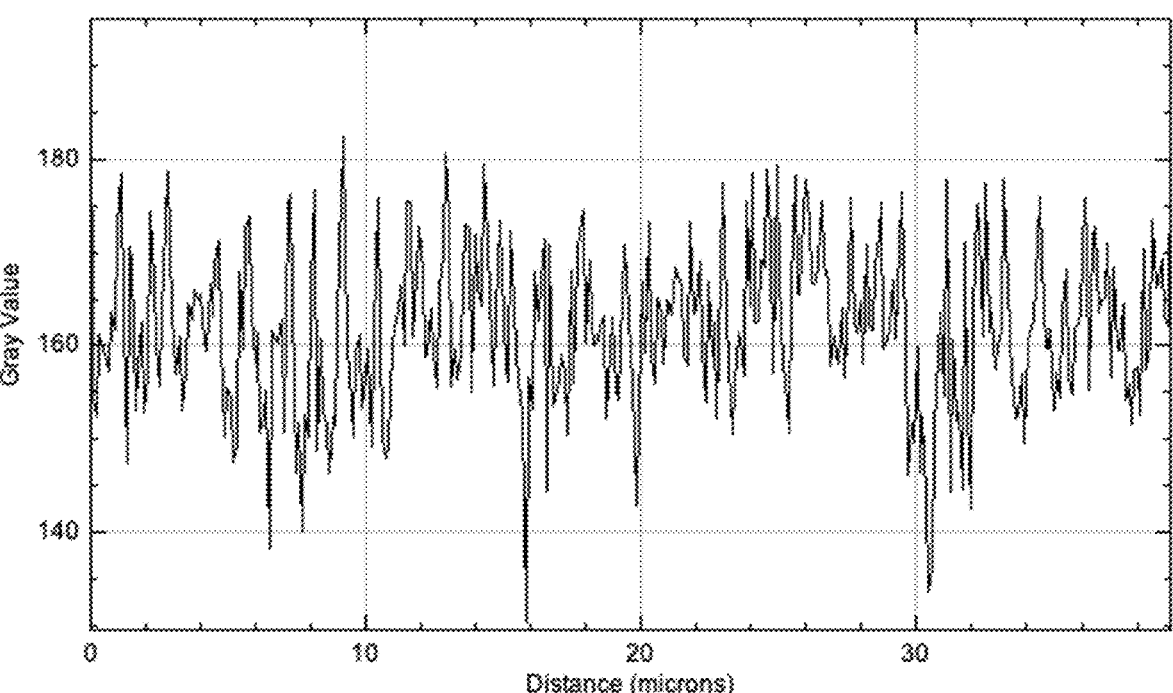
Figure 20A:
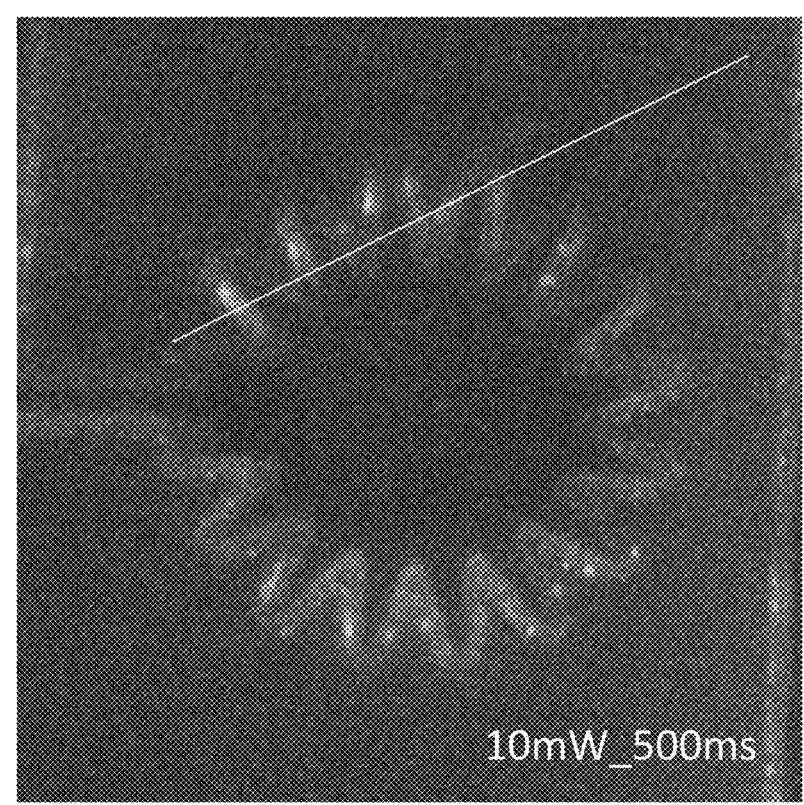
FIG. 20A and FIG. 20B show the results of a positive control in which a 12 mer DNA with an identical sequence was synthesized through conventional chemical activation on the side walls of the reaction sites. The signal/noise ratio is about 1.6, comparable with electrochemical activation. The overall higher background compared to previous electrochemical activation sample is due to the immersion oil used with the objective lens that has higher auto fluorescence level.
Figure 20B:
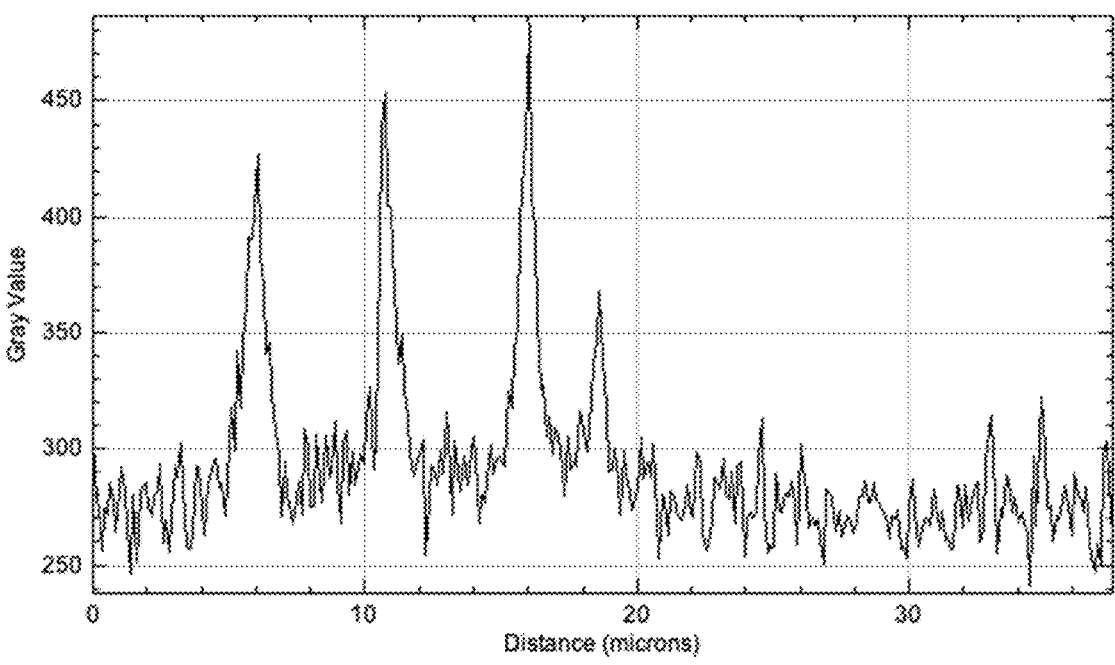

The hybridization protocol was as follows:
(1) Buffer Preparation
    Buffer (PB buffer): 100 mM NaCl, 10 mM Phosphate, pH7.4
    To prepare 100 mL of Phosphate Buffer:
        Prepare 80 mL of distilled water in a volumetric flask.
        Add 0.107 g of Sodium phosphate dibasic to the solution.
        Add 0.0296 g of Sodium phosphate monobasic to the solution.
        Adjust solution to final desired pH using HCl or NaOH
        Add distilled water until volume is 100 mL
        Add 0.5844 g NaCl
(2) DNA Target Solution
    Making 70 μM aliquot DNA target solution
        Add 1 mL of the buffer to dissolve a custom synthesized DNA target
        Divide the stock solution into 10 aliquots, store at −20° C.
(3) Dilute 70 μM Target DNA Solution into 1 μM Target Solution (Determined by UV Spectrometry))
    Add 100 μL of 70 μM target solution to 6.9 mL of buffer for 7 mL 1uM DNA target solution (4) Heat Up Target Solution to 95° C. for 5 Min to Remove any Possible Secondary Structures
(5) Freeze the Target Solution in Ice Water for 5 Min
(6) Immediately Perform Hybridization with Synthesized Probe for Overnight
    Heat up the chip to 75° C. and slowly cool down at a 1-5° C./min rate
(7) Brief Rinsing with PBS
(8) N$_2$ Dry and Imaging By the fact that fluorescent signal comes the second fluorescein labeled nucleotide, fluorescent signal can be only observed when the DNA with correct sequence successfully hybridize with the fluorescent target. FIG. 18A shows the fluorescent optical image of an electrochemically activated electrode and FIG. 18B shows the fluorescent intensity measurement across the reaction site. The fluorescent intensity measured (FIG. 18B) is about 300. Taking the background signal from the CCD detector as noise (150), the signal/noise ratio of the positive control is around 2 indicating successful synthesis of correct DNA synthesis. FIG. 18C and FIG. 18C show the fluorescent measurement result of another activated site with signal/noise ratio around 2. The signal/noise ratio between activated sites are comparable. FIG. 19A and FIG. 19B show the fluorescent measurement result of a site without activation on the same device as negative control. No obvious fluorescent signal is observed which indicates no complete DNA product is synthesized at this reaction site. FIG. 20A and FIG. 20B show the fluorescent measurement result of a positive control which the DNA sequence is synthesized through conventional chemical activation with signal/noise ratio around 1.6 which is comparable to electrochemical activation.

This example shows that electrochemical controlled 12 mer DNA synthesis was successfully verified by the hybridization test.

Materials and Methods

Device Fabrication:
    Quartz microscope coverslips (Electron Microscopy Sciences) were cleaned in hot 1:3 H$_2$O$_2$: H$_2$SO$_4$ solution (piranha clean) for 30 min, rinsed with milli-Q water. Three layers of photo resist (HMDS/LOR 3A/AZ3312) were spin coated at 4000 rpm for 40 seconds. The trench pattern was then defined with a GCA aligner and standard development procedure. Next, a 20-minute wet etch was applied with Ultra Etch 20:1 (KMG) to create 800 nm to 1000 nm wells. The exposed surface was cleaned by O$_2$ plasma for 1 minute and then 100 nm palladium was deposited at the bottom of the wells with electron beam evaporation method. The lift-off process was conducted by immersion in hot PG remover at 80° C. for 3 hr.

SiO$_2$ Surface Silanization:
    The SiO$_2$ surface was first cleaned with O$_2$ plasma for 1 minute and immediately immersed into linker solution (1.5% N-(3-triethoxysilylpropyl)-4-hydroxybutyramide, 5% water in ethanol) for 1.5 hour, rinsed with ethanol, and baked at 115 C in an oven for 20 minute.

Fluidic System
    The apparatus itself and a PDMS chamber compose the fluidic system. The apparatus was first adhered on a PCB board with PMMA. The selected electrodes for electrochemical reaction were bonded with a wedge-bonding machine; a PDMS chamber was molded in a 3D printed mold and fixed on the device with silicon gel and a mechanical clamp. An inlet and an outlet were attached to top of the chamber for reagent delivery. All chemicals needed for the synthesis were delivered to the chamber through a positive pressure with a syringe. All reactions were done in a glove box for controlled atmosphere.

DNA Synthesis:
    In this example, standard phosphoramadite chemistry was used for DNA synthesis. Solution comprising the first nucleotide (2 mM dT, 2 mM DCI activator in acetonitrile) was flowed through the camber for 10 minutes flowed by an acetonitrile flush; SCO oxidizer was then flowed through the chamber for 10 minutes followed by an acetonitrile flush; capping mix was the next reagent flowed through with a 10 minute reaction time and an acetonitrile flush was taken to flush all the residual chemicals. Next, for electrochemical detritylation/deblocking of the first nucleotide, the deblocking solution (50 mM hydroquinone/2.5 mM anthraquinone/0.1M tetraethylammonium p-toluenesulfonate) were flowed through the camber. A 3.6V potential was applied to selected electrode for electrochemical activation with a battery. The same procedure was followed for next cycle. At the end of synthesis, a deprotecting solution of ethylenediamine in ethanol (1:1) was flowed through the chamber for 5 min. Ethanol and milli-Q water flush were performed sequentially and the device was stored in dark for imaging.

Imaging:
    The synthesis result was analyzed with an epi-fluorescent microscope. A 488 nm laser was used for excitation source. Laser power was set at 5 mW and exposure time was 500 ms. The fluorescent intensity was analyzed with Nikon NIS-Elements software.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:
1. An apparatus for synthesizing a biopolymer, the apparatus comprising:
    (a) a substrate comprising a passivized top surface and a plurality of wells, wherein each of the plurality of wells comprises a first electrode disposed on the bottom of the well and a linker attached to the sides of the well; and
    (b) a fluidic chamber system disposed on the top surface of the substrate, wherein the diameter of a first well of the plurality of wells is about 1 μm to about 200 μm.
2. The apparatus according to claim 1, wherein the substrate is selected from glass, sputtered SiO$_2$, and SiO$_2$.
3. The apparatus according to claim 1, wherein the depth of the first well is from about 500 nm to about 500 μm.
4. The apparatus according to claim 1, wherein the depth of the first well is from about 1 μm to 10 μm.
5. The apparatus according to claim 1, further comprising a system for introducing and removing liquids from the first well.
6. A method for preparing an apparatus, comprising
    a. forming a plurality of wells on a substrate;
    b. applying a first electrode to the bottom of a first well of the plurality of wells;
    c. passivating a connection of the first electrode;
    d. attaching a linker to the sides of the first well; and
    e. affixing a fluidic chamber onto the substrate.

7. The method of claim 6, wherein step (a) comprises:
i. applying a photo resist onto the surface of the substrate to define the plurality of wells; and
ii. etching the substrate to create the plurality of wells.

8. The method of claim 7, wherein the substrate is selected from glass, sputtered $SiO_2$, and $SiO_2$.

9. The method of claim 7, wherein the first electrode is a material selected from gold, iridium, palladium, platinum or carbon.

10. The method of claim 7, wherein step (b) comprises physical vapor deposition of material selected from gold, iridium, palladium, platinum or carbon.

11. The method of claim 8, wherein step (b) further comprises removing the photo resist.

12. The method of claim 7, wherein step (c) comprises immersing the substrate from step (b) into a linker solution for a period of time; and removing the linker solution.

13. The method of claim 7, wherein the apparatus further comprises a system for introducing and removing liquids from the first well.

14. A method of synthesizing an oligonucleotide, the method comprising
(a) providing an apparatus, the apparatus comprising:
    i. a substrate comprising a passivized top surface and a plurality of wells, wherein each of the plurality of wells comprises a first electrode disposed on the bottom of the well and a linker attached to the sides of the well; and
    ii. a fluidic chamber system disposed on the top surface of the substrate;
(b) introducing a solution comprising a first nucleoside phosphoramidite monomer and an activator into a first well of the plurality of wells, wherein the first nucleoside phosphoramidite monomer comprises a 5'-protecting group, an acid sensitive protecting group and optionally a base sensitive protecting group, and wherein the first nucleoside phosphoramidite monomer reacts with the linker attached to the side walls of the first well to form a linked nucleoside through a phosphite triester;

(c) removing the solution from step (b) from the first well;
(d) introducing a solution comprising a capping reagent into the well, wherein the capping reagent reacts with any unreacted linker from step (b) to form a capped linker;
(e) removing the solution from step (d) from the first well;
(f) introducing a solution comprising an oxidant into the first well, wherein the oxidant converts the phosphite triester of the linked nucleoside to a phosphate triester;
(g) removing the solution from step (f) from the first well;
(h) introducing a solution comprising a first deprotecting reagent into the first well, wherein an electrochemically generated proton in the first deprotecting reagent removes the 5'-protecting group;
(i) removing the solution from step (h) from the first well;
(j) repeating steps (b) through (i) to synthesize a protected oligonucleotide; and
(k) introducing a solution comprising a second deprotecting reagent into the first well, wherein the second deprotecting agent removes the protecting groups on the oligonucleotide.

15. The method of claim 14, wherein the capping reagent is acetic anhydride.

16. The method of claim 14, wherein the capped linker comprises an acetate group.

17. The method of claim 14, wherein the oxidant is (1S)-(+)-(10-camphorsulfonyl)-oxaziridine (CSO).

18. The method of claim 14, wherein the first deprotecting reagent removes a 5'-dimethyltrityl group.

19. The method of claim 18, wherein the first deprotecting reagent is hydroquinone.

20. The method of claim 14, wherein the second deprotecting reagent removes a phosphate protecting group.

21. The method of claim 14, wherein the second deprotecting reagent removes the base protecting groups.

22. The method of claim 20, wherein the second deprotecting reagent is ethylenediamine.

* * * * *